United States Patent
Sieweke

(10) Patent No.: US 10,709,762 B2
(45) Date of Patent: Jul. 14, 2020

(54) USE OF M-CSF FOR PREVENTING OR TREATING MYELOID CYTOPENIA AND RELATED COMPLICATIONS

(71) Applicants: INSERM (INSTITUT NATIONAL DE LA SANTE ET DE LA RECHERCHE MÉDICALE), Paris (FR); CENTRE NATIONAL DE LA RECHERCHE SCIENTIFIQUE (CNRS), Paris (FR); UNIVSERSITÉ D'AIX MARSEILLE, Marseilles (FR)

(72) Inventor: Michael Sieweke, Marseilles (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE D'AIX-MARSEILLE, Marseilles (FR)

( * ) Notice: Subject to any disclaimer, the term of this patent is extended or adjusted under 35 U.S.C. 154(b) by 264 days.

(21) Appl. No.: 14/782,612

(22) PCT Filed: Apr. 9, 2014

(86) PCT No.: PCT/EP2014/057191
§ 371 (c)(1),
(2) Date: Oct. 6, 2015

(87) PCT Pub. No.: WO2014/167018
PCT Pub. Date: Oct. 16, 2014

(65) Prior Publication Data
US 2016/0045567 A1     Feb. 18, 2016

(30) Foreign Application Priority Data

Apr. 9, 2013   (EP) ..................... 13305464

(51) Int. Cl.
| | |
|---|---|
| *A61K 38/19* | (2006.01) |
| *A61K 35/51* | (2015.01) |
| *C12N 5/00* | (2006.01) |
| *A61P 37/04* | (2006.01) |
| *A61K 35/14* | (2015.01) |
| *A61K 35/28* | (2015.01) |
| *A61K 38/20* | (2006.01) |
| *C12N 5/0789* | (2010.01) |
| *A61K 35/12* | (2015.01) |
| *C12N 5/0787* | (2010.01) |

(52) U.S. Cl.
CPC ............ *A61K 38/193* (2013.01); *A61K 35/14* (2013.01); *A61K 35/28* (2013.01); *A61K 35/51* (2013.01); *A61K 38/20* (2013.01); *A61P 37/04* (2018.01); *C12N 5/00* (2013.01); *C12N 5/0647* (2013.01); *A61K 2035/124* (2013.01); *C12N 2501/22* (2013.01); *Y02A 50/475* (2018.01); *Y02A 50/481* (2018.01)

(58) Field of Classification Search
None
See application file for complete search history.

(56) References Cited

U.S. PATENT DOCUMENTS

| | | |
|---|---|---|
| 5,649,904 A | 7/1997 | Gianni |
| 2006/0134783 A1* | 6/2006 | Fong ................. C12N 5/0647 435/372 |
| 2009/0148405 A1 | 6/2009 | Hochrein et al. |

OTHER PUBLICATIONS

Kolchanov, (1988), Journal of Molecular Evolution, vol. 27, pp. 154-162.*
Pasquo, (2012), PLoS ONE, vol. 7, Issue 2, e32555.*
Hidaka et al. (2001), Jpn. J. Cancer, vol. 92, pp. 1251-1258.*
Masaoka et al. (1990), British J. Haematology, vol. 76, 501-505.*
Yu et al., JBC, vol. 287, No. 17, pp. 13694-13704 (Year: 2012).*
Pixley et al., Trends in Biology, vol. 14, No. 11, pp. 628-638 (Year: 2004).*
Rathinann et al. Blood, vol. 118 (11), pp. 3119-3128. (Year: 2011).*
Sarrazin et al., Cell, vol. 138, pp. 1-9. (supplemental Data) (Year: 2009).*
Sarrazin et al., "MafB Restricts M-CSF-Dependent Myeloid Commitment Divisions of Hematopoietic Stem Cells", CELL, Jul. 2009, pp. 300-313, vol. 138, No. 2.
Sarrazin et al., "Integration of cytokine and transcription factor signals in hematopoietic stem cell commitment", Seminars in Immunology, Oct. 2011, pp. 326-334, vol. 23, No. 5.
Hamilton et al., "Colony stimulating factors and myeloid cell biology in health and disease", Trends in Immunology, Feb. 2013, pp. 81-89, vol. 34, No. 2.
Ohno et al., "Human urinary macrophage colony-stimulating factor reduces the incidence and duration of febrile neutropenia and shortens the period required to finish three courses of intensive consolidation therapy in acute myeloid leukemia: a double-blind controlled study", Journal of Clinical Oncology, vol. 15, No. 8, Aug. 1997, pp. 2954-2965.

* cited by examiner

*Primary Examiner* — Joanne Hama
*Assistant Examiner* — Jegatheesan Seharaseyon
(74) *Attorney, Agent, or Firm* — W&C IP

(57) ABSTRACT

The invention relates to methods and compositions comprising a macrophage colony stimulating factor (M-CSF) polypeptide or an agonist of the M-CSF receptor for preventing or treating myeloid cytopenia and related complications (such as infections) in a patient in need thereof (such as a patient undergoing hematopoietic stem cell transplantation).

10 Claims, 11 Drawing Sheets
Specification includes a Sequence Listing.

a b c

Figure 7C:
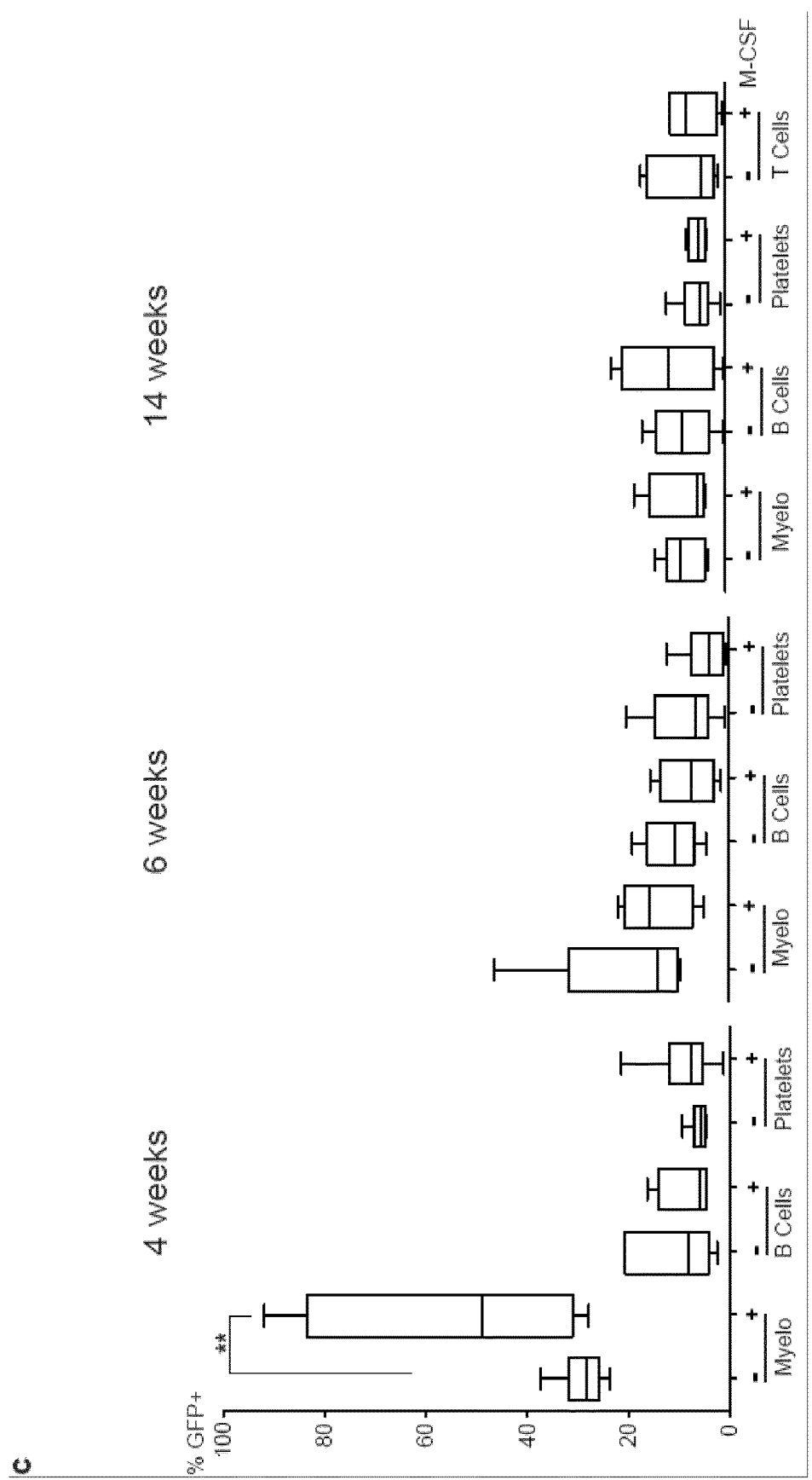

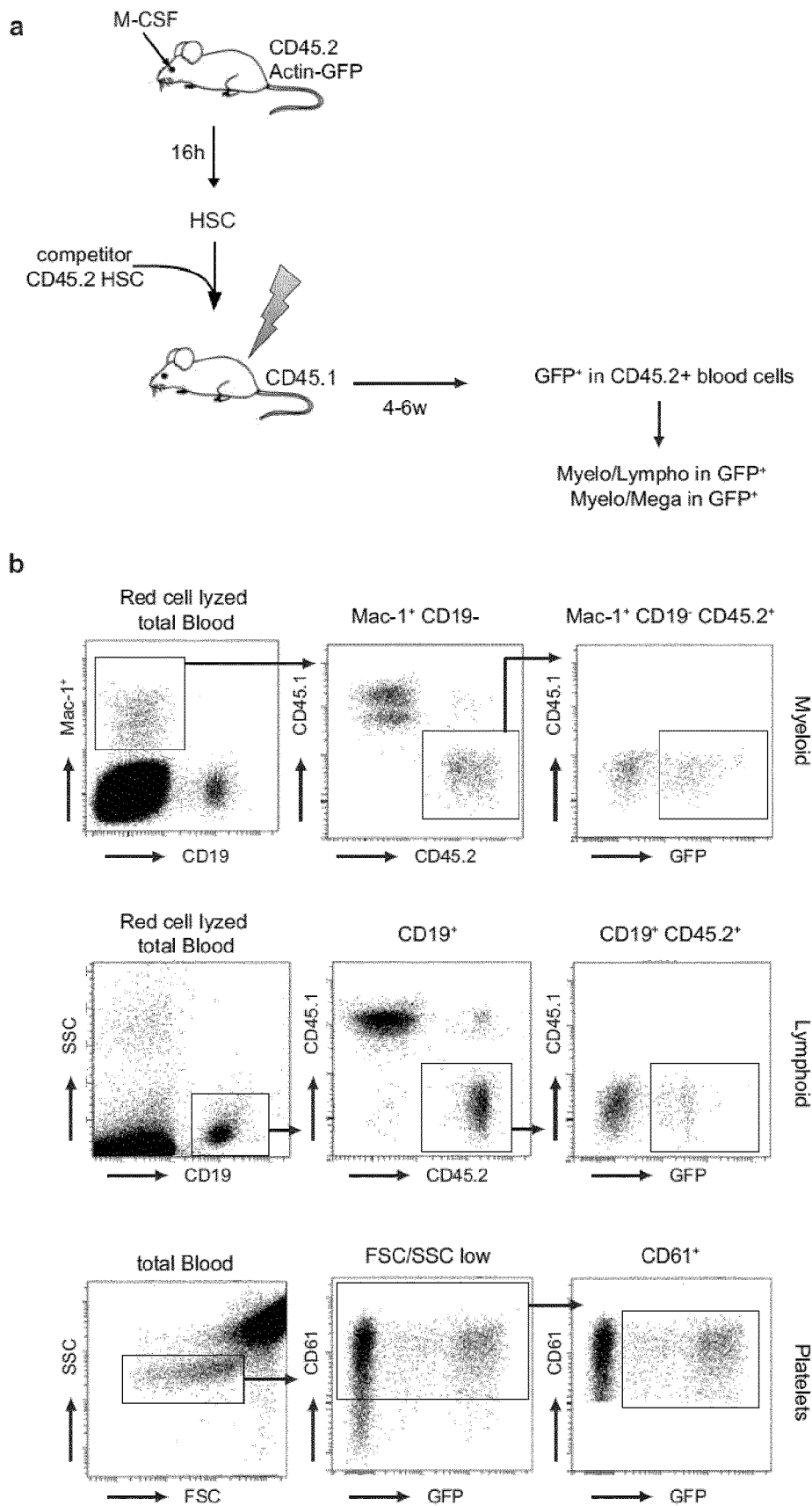
Figure 7A&B

USE OF M-CSF FOR PREVENTING OR TREATING MYELOID CYTOPENIA AND RELATED COMPLICATIONS

FIELD OF THE INVENTION

The invention relates to the field of oncology, cancer therapy and immunodeficiencies caused by myeloid cytopenia. More particularly, the invention relates to methods and compositions comprising a macrophage colony stimulating factor (M-CSF) polypeptide or an agonist of the M-CSF receptor for preventing or treating myeloid cytopenia and related complications (such as infections) in a patient in need thereof (such as a patient undergoing hematopoietic stem cell transplantation).

BACKGROUND OF THE INVENTION

Hematopoietic stem cell transplantation (HSCT) which consists of the infusion of hematopoietic stem cells can cure a wide variety of diseases, including leukemia, lymphoma, myeloproliferative disorders, myelodysplastic syndrome (MDS), bone marrow (BM) failure syndromes, congenital immunodeficiencies, enzyme deficiencies and hemoglobinopathies.

Despite considerable progress in the management of the complications of HSCT, infection (additionally to regimen-related toxicity (RRT) and graft-versus-host-disease (GVHD) remains an important cause of post-transplant morbidity and mortality, mainly after allogeneic HSCT. The major advances in the management of infectious complications have come from better understanding of the mechanisms of the complex depression of immunity observed during the first months after transplant and their role in the predisposition to given infections, and also from well-designed therapeutic trials. Although the proportion of infectious deaths after allogeneic HSCT has decreased over the last two decades, much remains to be done to further decrease this risk and implement more efficient preventive and prophylactic strategies adapted to this high-risk population.

Moreover, even though the risk of infectious deaths is much lower after autologous transplant, the risks of the procedure are greater than those of conventional chemotherapy, and preventive policies should be implemented in any transplant program.

The spectrum of pathogens to which HSCT recipients are most susceptible follows a time line corresponding to the predominant immune defects. In the first month of HSCT, neutropenia is the principal host defense defect, predisposing patients to bacterial, fungal, and viral infections. After HSCT, qualitative dysfunction of phagocytes persists because of corticosteroids and other immunosuppressive agents. The risk of infection by opportunistic viruses, bacteria and filamentous fungi during this period is strongly associated with the severity of GVHD and the requirement for potent immunosuppressive regimens.

New approaches have thus been developed to minimize the likelihood of infections. For instance, granulocyte colony-stimulating factor [G-CSF or filgastrim] or granulocyte-macrophage colony-stimulating factor [GM-CSF or sargramostim] have been used since they shorten the duration of neutropenia after HSCT; however, no data were found that indicate whether these growth factors effectively reduce the attack rate of opportunistic diseases (including bacterial infections or fungal infections) and thus reduce mortality.

Therefore, the routine use of these growth factors after HSCT is controversial and no recommendation for their use can be made. It results that means useful for effectively preventing infections among hematopoietic stem cell transplantation (HSCT) recipients are still highly needed in order to improve their survival after HSCT.

Moreover, under stress conditions such as infection or inflammation the body rapidly needs to generate new blood cells that are adapted to the challenge. Haematopoietic cytokines are known to affect survival, expansion and differentiation of lineage committed progenitors[1,2] but it has been debated whether long term haematopoietic stem cells (HSC) are susceptible to direct lineage-specifying effects of cytokines to produce a specific type of progenitors. Although genetic changes in transcription factor balance can sensitize HSC to cytokine instruction[3], the initiation of HSC commitment is generally thought to be triggered by stochastic fluctuation in cell intrinsic regulators such as lineage specific transcription factors[4,5,6,7], leaving cytokines to ensure survival and proliferation of the progeny cells at later differentiation stages[8,9].

SUMMARY OF THE INVENTION

In a first aspect, the invention relates to a macrophage colony stimulating factor (M-CSF) polypeptide or an agonist of the M-CSF receptor for use in a method for transiently providing granulocyte/monocyte progenitor cells (GMP) in a patient in need thereof.

In a second aspect, the invention relates to a M-CSF polypeptide or an agonist of the M-CSF receptor for use in preventing or treating myeloid cytopenia and related complications in a patient in need thereof.

In a third aspect, the invention also relates to a hematopoietic stem cell graft primed in the presence of a M-CSF polypeptide or an agonist of the M-CSF receptor.

In a fourth aspect, the invention also relates to a hematopoietic stem cell graft primed in the presence of a M-CSF polypeptide or an agonist of the M-CSF receptor for use in preventing or treating myeloid cytopenia and related complications in a patient undergoing HSCT.

In a fifth aspect, the invention further relates to a kit-of-part composition comprising (i) a hematopoietic stem cell graft and (ii) a M-CSF polypeptide or an agonist of the M-CSF receptor for simultaneous and/or subsequent use in preventing or treating myeloid cytopenia and related complications in a patient undergoing HSCT.

In another aspect, the invention further relates to a method for improving the survival time of a patient undergoing HSCT, comprising a step of administering to said patient a therapeutically effective amount of a M-CSF polypeptide or an agonist of M-CSF receptor simultaneously and/or subsequently to the HSCT.

In a further aspect, the invention relates to a method for improving the survival time of a patient of a patient undergoing HSCT, comprising a step of administering to said patient a therapeutically effective amount of hematopoietic stem cell graft primed in the presence of a M-CSF polypeptide or an agonist of the M-CSF receptor.

DETAILED DESCRIPTION OF THE INVENTION

The inventors have now demonstrated that macrophage colony stimulating factor (M-CSF), a myeloid cytokine released during infection and inflammation can directly induce the myeloid master regulator PU.1 and instruct myeloid cell fate change in HSC, independently of selective survival or proliferation. Video imaging and single cell gene expression analysis revealed that stimulation of highly purified HSC with M-CSF in culture resulted in activation of the PU.1 promoter and an increased number of PU.1+ cells with myeloid gene signature and differentiation potential. In vivo, high systemic levels of M-CSF directly stimulated M-CSF receptor dependent activation of endogenous PU.1 protein in single HSC and induced a PU.1 dependent myeloid differentiation preference.

They have indeed demonstrated that only M-CSF (comparatively to GM-CSF and G-CSF) can act directly on HSC in vitro and in vivo to instruct a change of cell identity and thus to specifically and transiently provide increased granulocyte/monocyte progenitor cells (GMP) without compromising stem cell activity. This newly identified property of M-CSF is of major interest for ameliorating myeloid cytopenia, particularly to protect patients from infection after stem cell transplantation and thus for preventing or treating myeloid cytopenias (e.g. neutropenia) and related complications in a patient in need thereof such as a patient undergoing HSCT, and more particularly bacterial and/or fungal infections, which occur for instance after HSCT while the immune system is not yet reestablished in the recipient for fighting these opportunistic infections.

Therapeutic Methods and Uses

The invention provides methods and compositions (such as pharmaceutical and kit- of part compositions) for use in transiently providing granulocyte/monocyte progenitor cells (GMP) in a patient in need thereof (such as a patient undergoing HSCT). The invention also provides methods and compositions for use in preventing or treating myeloid cytopenia and related complications in a patient in need thereof.

In a first aspect, the invention relates to a macrophage colony stimulating factor (M-CSF) polypeptide or an agonist of the M-CSF receptor for use in a method for transiently providing granulocyte/monocyte progenitor cells (GMP) in a patient in need thereof.

As used herein, the term "transiently providing" in the context of cells refers to increase transitory (i.e. during a limited time period, preferably during one month after HSCT) in the number of a characteristic cell type, or cell types, from an initial population of cells. Accordingly, the transiently providing cells of interest (i.e. granulocyte/macrophage progenitor cells) are produced by in vivo differentiation of the initial population of cells (i.e. a HSC graft administered to the patient undergoing HSCT). It should further be noted that the M-CSF polypeptide or the agonist of the M-CSF receptor (such as the IL-34 polypeptide) specifically and transiently provides granulocyte/macrophage progenitor cells and do not provide other cells including lymphoid cells (e.g. lymphoid progenitor cells). Accordingly, the majority of HSC administered to the patient undergoing HSCT specifically and transiently gave rise to granulocyte/macrophage progenitor cells but not to other cells type in particular lymphoid progenitor cells (which would bear the risk of GVHD). Indeed, "graft-versus-host disease" (also called "GVH" or "GVHD") refers to a cellular response that occurs when lymphocytes of a different MHC class are introduced into a host, resulting in the reaction of the lymphocytes against the host.

As used herein, the terms "granulocyte/macrophage progenitor cells" or "GMP" refer to cells derived from common myeloid progenitor cells, and characterized by its capacity to give rise to granulocyte and macrophage cells, but which does not typically give rise to erythroid cells or megakaryocytes of the myeloid lineage.

In a second aspect, the invention relates to a M-CSF polypeptide or an agonist of the M-CSF receptor for use in preventing or treating myeloid cytopenia and related complications in a patient in need thereof.

As used herein, the terms "macrophage colony stimulating factor polypeptide" or "M-CSF polypeptide" (also known as CSF-1, for "colony stimulating factor 1 polypeptide") refer to any native or variant (whether native or synthetic) cytokine which controls the production, differentiation, and function of macrophages. The term includes naturally occurring M-CSF variants and modified forms thereof. Thus, three distinct variant M-CSF isoforms produced through alternative mRNA splicing have been described, respectively a M-CSF[alpha] variant which refers to a protein of 256 amino acids provided in the UniProt Uniparc database under accession number UPI0000D61F83, a M-CSF[beta] variant which refers to a protein of 554 amino acids provided in the GenPept database under accession number NP_000748.3 and is encoded by the nucleic acid sequence provided in the GenBank database under accession number NM_000757.5, and a M-CSF[gamma] variant which refers to a protein of 438 amino acids provided in the GenPept database under accession number NP_757349.1 and is encoded by the nucleic acid sequence provided in the GenBank database under accession number NM_172210.2.

In one embodiment, the M-CSF polypeptide is the human isoform M-CSF[alpha] of 256 amino acids provided in the UniProt/Uniparc database under accession number UPI0000D61F83 and is shown as follows (SEQ ID NO: 1) or a polypeptide having a sequence at least 80%, 85%, 90%, 95%, 96%, 97%, 98% or 99% identical to the sequence

```
SEQ ID NO: 1:
MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRFR

DNTPNAIAIVQLQELSLRLKSCFTKDYEEHDKACVRTFYETPLQLLEKVK

NVFNETKNLLDKDWNIFSKNCNNSFAECSSQGHERQSEGSFSPQLQESVF

HLLVPSVILVLLAVGGLLFYRWRRRSHQEPQRADSPLEQPEGSPLTQDDR

QVELPV
```

In one embodiment, the M-CSF polypeptide is the human isoform M-CSF[beta] of 554 amino acids provided in the GenBank database under accession number NP_000748.3 and is shown as follows (SEQ ID NO: 2) or a polypeptide having a sequence at least 80%, 85%, 90%, 95%, 96%, 97%, 98% or 99% identical to the sequence SEQ ID NO: 2:

```
MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRFR

DNTPNAIAIVQLQELSLRLKSCFTKDYEEHDKACVRTFYETPLQLLEKVK

NVFNETKNLLDKDWNIFSKNCNNSFAECSSQDVVTKPDCNCLYPKAIPSS

DPASVSPHQPLAPSMAPVAGLTWEDSEGTEGSSLLPGEQPLHTVDPGSAK

QRPPRSTCQSFEPPETPVVKDSTIGGSPQPRPSVGAFNPGMEDILDSAMG

TNWVPEEASGEASEIPVPQGTELSPSRPGGGSMQTEPARPSNFLSASSPL
```

-continued

PASAKGQQPADVTGTALPRVGPVRPTGQDWNHTPQKTDHPSALLRDPPEP

GSPRISSLRPQGLSNPSTLSAQPQLSRSHSSGSVLPLGELEGRRSTRDRR

SPAEPEGGPASEGAARPLPRFNSVPLTDTGHERQSEGSSSPQLQESVFHL

LVPSVILVLLAVGGLLFYRWRRRSHQEPQRADSPLEQPEGSPLTQDDRQV

ELPV

In one embodiment, the M-CSF polypeptide is the human isoform M-CSF[gamma] of 438 amino acids provided in the GenBank database under accession number NP_757349.1_and is shown as follows (SEQ ID NO: 3) or a polypeptide having a sequence at least 80%, 85%, 90%, 95%, 96%, 97%, 98% or 99% identical to the sequence SEQ ID NO: 3:

MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRFR

DNTPNAIAIVQLQELSLRLKSCFTKDYEEHDKACVRTFYETPLQLLEKVK

NVFNETKNLLDKDWNIFSKNCNNSFAECSSQDVVTKPDCNCLYPKAIPSS

DPASVSPHQPLAPSMAPVAGLTWEDSEGTEGSSLLPGEQPLHTVDPGSAK

QRPPRSTCQSFEPPETPVVKDSTIGGSPQPRPSVGAFNPGMEDILDSAMG

TNWVPEEASGEASEIPVPQGTELSPSRPGGGSMQTEPARPSNFLSASSPL

PASAKGQQPADVTGHERQSEGSSSPQLQESVFHLLVPSVILVLLAVGGLL

FYRWRRRSHQEPQRADSPLEQPEGSPLTQDDRQVELPV

As used herein, the term "polypeptide" refers to a polymer of amino acid residues joined by peptide bonds, whether produced naturally or synthetically, having no specific length. Thus, peptides, oligopeptides and proteins are included in the definition of polypeptide and these terms are used interchangeably throughout the specification, as well as in the claims. The term polypeptide does not exclude post-translational modifications that include but are not limited to phosphorylation, acetylation, glycosylation and the like. The term also applies to amino acid polymers in which one or more amino acid residue is an artificial chemical mimetic of a corresponding naturally occurring amino acid, as well as to naturally occurring amino acid polymers and non-naturally occurring amino acid polymer.

The term "M-CSF polypeptide" is herein defined as including the naturally occurring human polypeptide M-CSF and naturally-occurring allelic variations of the polypeptide. Allelic variations are naturally-occurring base changes in the species population which may or may not result in an amino acid change in a polypeptide or protein. Additionally, the M-CSF polypeptides according to the invention not only encompass polypeptides comprising or consisting of full-length M-CSF and variants thereof, but also polypeptides consisting of fragments thereof, provided the fragments are biologically active. Additionally included in this definition are both recombinant and synthetic versions of the polypeptide M-CSF, which may contain induced modifications in the polypeptide and DNA sequences thereof. Accordingly, the term M-CSF polypeptide intends to encompass the functional equivalents of the M-CSF polypeptides encoded by the sequence SEQ ID NO: 1, SEQ ID NO: 2 or SEQ ID NO: 3.

As used herein, a "functional equivalent" refers to a molecule (e.g. a recombinant polypeptide) that retains the biological activity and the specificity of the parent polypeptide. Therefore, the term "functional equivalent of the M-CSF polypeptide" includes variants and fragments of the polypeptide to which it refers (i.e. the M-CSF polypeptide) provided that the functional equivalents exhibit at least one, preferably all, of the biological activities of the reference polypeptide, as described below.

A polypeptide "variant" refers to a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the frame of the present application, the percentage of identity is calculated using a global alignment (i.e., the two sequences are compared over their entire length). Methods for comparing the identity and homology of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Polypeptides consisting of an amino acid sequence "at least 80%, 85%, 90%, 95%, 96%, 97%, 98% or 99% identical" to a reference sequence may comprise mutations such as deletions, insertions and/or substitutions compared to the reference sequence. The polypeptide consisting of an amino acid sequence at least 80%, 85%, 90%, 95%, 96%, 97%, 98% or 99% identical to a reference sequence may correspond to an allelic variant of the reference sequence. It may for example only comprise substitutions compared to the reference sequence. The substitutions preferably correspond to conservative substitutions as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |

| Conservative substitutions | Type of Amino Acid |
|---|---|
| Asp, Glu | Amino acids with acidic side chains |
| Lys, Arg, His | Amino acids with basic side chains |
| Gly | Neutral side chain |

A polypeptide "fragment", as used herein, refers to a biologically active polypeptide that is shorter than a reference polypeptide (e.g. a fragment of the M-CSF polypeptide). Thus, the polypeptide according to the invention encompasses polypeptides comprising or consisting of fragments of M-CSF, provided the fragments are biologically active.

In the frame of the invention, the biologically active fragment may for example comprise at least 150, 175, 200, 225, 250, 275, 300, 325, 350, 375, 400, 425, 450, 475, 500, 525 or 550 consecutive amino acids of the M-CSF polypeptide.

As described above the three M-CSF isoforms are synthesized from a full-length and a truncated precursor. It should be further noted that the N-terminal 150 amino acids of precursors are identical and sufficient for in vitro biological activity as described in Pixley et al. 2004 Trends Cell Biol. 2004 November; 14(11):628-38). Indeed, amino acids 1-150 of all three mature forms of M-CSF are identical and are believed to contain sequences essential for biological activity of M-CSF. Accordingly, a biologically active fragment of the MCSF-polypeptide is a N-terminal fragment comprising at least 150 amino acids.

In one embodiment, the M-CSF polypeptide is a recombinant 156 amino acid polypeptide of murine M-CSF and is shown as follows (SEQ ID NO: 4):

MKEVSEHCSHMIGNGHLKVLQQLIDSQMETSCQIAFEFVDQEQLDDPVCY

LKKAFFLVQDIIDETMRFKDNTPNANATERLQELSNNLNSCFTKDYEEQN

KACVRTFHETPLQLLEKIKNFFNETKNLLEKDWNIFTKNCNNSFAKCSSR

DVVTKP

In one particular embodiment, the M-CSF polypeptide comprises or consists of a 150 amino acid polypeptide of human M-CSF and is shown as follows (SEQ ID NO: 5):

MTAPGAAGRCPPTTWLGSLLLLVCLLASRSITEEVSEYCSHMIGSGHLQS

LQRLIDSQMETSCQITFEFVDQEQLKDPVCYLKKAFLLVQDIMEDTMRFR

DNTPNAIAIVQLQELSLRLKSCFTKDYEEHDKACVRTFYETPLQLLEKVK

By "biological activity" of M-CSF or a fragment thereof is meant (i) the capacity to induce the myeloid differentiation of hematopoietic stem cell (HSC) (more particularly the myelo-monocytic differentiation as described in the Section Examples; i.e. the capacity to induce the increased production of GMP by HSC); and/or (ii) the capacity to induce the expression of the transcription factor PU.1 (as described in the Section Examples); and/or (iii) the capacity to treat or prevent myeloid cytopenia and related complications (such as infections).

The skilled in the art can easily determine whether a fragment of the M-CSF polypeptide is biologically active. To check whether the newly generated polypeptides induce the in vitro or in vivo myeloid differentiation of HSC and/or induce the expression of the transcription factor PU.1, a FACS analysis, a qRT-PCR analysis or a single cell gene expression profiling (see in Example section) may be performed for each polypeptide. Moreover, to check whether the newly generated polypeptides treat or prevent myeloid cytopenia and related complications (such as infections), mouse model of bone marrow transplantation (BMT) and graft-versus-host disease may be used. Additionally, a time-course and a dose-response performed in vitro or in vivo (e.g. by using a murine model of BMT and GVHD) will determine the optimal conditions for each polypeptide.

As used herein, the term "agonist of the M-CSF receptor" refers to any compound synthetic or natural (for instance a polypeptide) capable of binding to the M-CSF receptor (also known as CD115, which is a cell-surface protein encoded, in humans, by the CSF1R gene) present on hematopoietic stem cells and hematopoietic precursor cells and stimulating the production of myeloid cells, monocytes, macrophages or related cells of mononuclear phagocyte system, such as microglia and Langerhans cells. In one embodiment, the M-CSF receptor ligand is a human polypeptide.

In a preferred embodiment, the agonist of the M-CSF receptor is the IL34 polypeptide.

As used herein, the terms "Interleukin-34 polypeptide" or "IL-34 polypeptide" are well known in the art and refer to a cytokine that promotes the proliferation, survival and differentiation of monocytes and macrophages. The naturally occurring human IL-34 protein has an amino acid sequence of 242 amino acids provided in the UniProt database under accession number Q6ZMJ4 and is shown as follows (SEQ ID NO: 6) or a polypeptide having a sequence at least 80%, 85%, 90%, 95%, 96%, 97%, 98% or 99% identical to the sequence SEQ ID NO: 6:

MPRGFTWLRYLGIFLGVALGNEPLEMWPLTQNEECTVTGFLRDKLQYRSR

LQYMKHYFPINYKISVPYEGVFRIANVTRLQRAQVSERELRYLWVLVSLS

ATESVQDVLLEGHPSWKYLQEVETLLLNVQQGLTDVEVSPKVESVLSLLN

APGPNLKLVRPKALLDNCFRVMELLYCSCCKQSSVLNWQDCEVPSPQSCS

PEPSLQYAATQLYPPPPWSPSSPPHSTGSVRPVRAQGEGLLP

As previously described for the M-CSF polypeptide, the term IL-34 polypeptide intends to encompass the functional equivalents of the IL-34 polypeptide encoded by the sequence SEQ ID NO: 6.

In one embodiment, the polypeptides of the invention may comprise a tag. A tag is an epitope-containing sequence which can be useful for the purification of the polypeptides. It is attached to by a variety of techniques such as affinity chromatography, for the localization of said polypeptide within a cell or a tissue sample using immuno labeling techniques, the detection of said polypeptide by immunoblotting etc. Examples of tags commonly employed in the art are the GST (glutathion-S-transferase)-tag, the FLAG™-tag (an affinity tag), the STREP-TAG™ (an affinity tag), V5 tag, myc tag, His tag (which typically consists of six histidine residues), etc.

In another embodiment, the polypeptides of the invention may comprise chemical modifications improving their stability and/or their biodisponibility. Such chemical modifications aim at obtaining polypeptides with increased protection of the polypeptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:

- replacement(s) of an amino acid with a modified and/or unusual amino acid, e.g. a replacement of an amino acid with an unusual amino acid like Nle, Nva or Orn; and/or
- modifications to the N-terminal and/or C-terminal ends of the peptides such as e.g. N-terminal acylation (preferably acetylation) or desamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids.
- chirality changes such as e.g. replacement of one or more naturally occurring amino acids (L enantiomer) with the corresponding D-enantiomers;
- retro-inversions in which one or more naturally-occurring amino acids (L-enantiomer) are replaced with the corresponding D-enantiomers, together with an inversion of the amino acid chain (from the C-terminal end to the N-terminal end);
- azapeptides, in which one or more alpha carbons are replaced with nitrogen atoms; and/or
- betapeptides, in which the amino group of one or more amino acid is bonded to the β carbon rather than the α carbon.

Another strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VECTRAMED (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the polypeptides described herein for therapeutic delivery.

In still another embodiment, the polypeptides of the invention may be fused to a heterologous polypeptide (i.e. polypeptide derived from an unrelated protein, for example, from an immunoglobulin protein).

As used herein, the terms "fused" and "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. For instance, a recombinant fusion protein may be a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence.

As used herein, the term "M-CSF fusion protein" refers to a polypeptide comprising the M-CSF polypeptide or a functional equivalent thereof fused to heterologous polypeptide. The M-CSF fusion protein will generally share at least one biological property in common with the M-CSF polypeptide (as described above).

An example of a M-CSF fusion protein is a M-CSF immunoadhesin.

As used herein, the term "immunoadhesin" designates antibody-like molecules which combine the binding specificity of a heterologous protein (an "adhesin") with the effector functions of immunoglobulin constant domains.

Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The immunoglobulin sequence preferably, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In one embodiment, the Fc region is a native sequence Fc region. In another embodiment, the Fc region is a variant Fc region. In still another embodiment, the Fc region is a functional Fc region. The M-CSF sequence portion and the immunoglobulin sequence portion of the M-CSF immunoadhesin may be linked by a minimal linker. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

Another example of a M-CSF fusion protein is a fusion of the M-CSF polypeptide with human serum albumin-binding domain antibodies (ALBUDAB™) according to the ALBUDAB™ Technology Platform as described in Konterman et al. 2012, ALBUDAB™ Technology Platform-Versatile Albumin Binding Domains for the Development of Therapeutics with Tunable Half-Lives.

The polypeptides of the invention may be produced by any suitable means, as will be apparent to those of skill in the art. In order to produce sufficient amounts of M-CSF polypeptides for use in accordance with the invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E. coli*.

Moreover, it should be noted that the majority of protein-based biopharmaceuticals bare some form of post-translational modification which can profoundly affect protein properties relevant to their therapeutic application. Protein glycosylation represents the most common modification (about 50% of human proteins are glycosylated). Glycosylation can introduce considerable heterogeneity into a protein composition through the generation of different glycan structures on the proteins within the composition. Such glycan structures are made by the action of diverse enzymes of the glycosylation machinery as the glycoprotein transits the Endoplasmatic Reticulum (ER) and the Golgi-Complex (glycosylation cascade). The nature of the glycan structure(s) of a protein has impact on the protein's folding, stability, life time, trafficking, pharmaco-dynamics, pharmacokinetics and immunogenicity. The glycan structure has great impact on the protein's primary functional activity. Glycosylation can affect local protein structure and may help to direct the folding of the polypeptide chain. One important kind of glycan structures are the so called N-glycans. They are generated by covalent linkage of an oligosaccharide to the amino (N)-group of asparagin residues in the consensus sequence NXS/T of the nascent polypeptide chain. N-glycans may further participate in the sorting or directing of a protein to its final target: the N-glycan of an antibody, for example, may interact with complement components. N-glycans also serve to stabilize a glycoprotein, for example, by enhancing its solubility, shielding hydrophobic patches on its surface, protecting from proteolysis, and directing intra-chain stabilizing interactions. Glycosylation may regulate protein half-life, for example, in humans the presence of terminal sialic acids in N-glycans may increase the half-life of proteins, circulating in the blood stream.

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N~linked glycoproteins.

A number of yeasts, for example, *Pichia pastoris*, *Yarrowia lipolytica* and *Saccharomyces cerevisiae* are recently under development to use the advantages of such systems but to eliminate the disadvantages in respect to glycosylation. Several strains are under genetical development to produce defined, human-like glycan structures on a protein. Methods for genetically engineering yeast to produce human-like N-glycans are described in U.S. Pat. Nos. 7,029, 872 and 7,449,308 along with methods described in U.S. Published Application Nos. 20040230042, 20050208617, 20040171826, 20050208617, and 20060286637. These methods have been used to construct recombinant yeast that can produce therapeutic glycoproteins that have predominantly human-like complex or hybrid N-glycans thereon instead of yeast type N-glycans. As previously described, human-like glycosylation is primarily characterized by "complex" N-glycan structures containing N-acetylglucosamine, galactose, fucose and/or N-acetylneuraminic acid. Thus, several strains of yeasts have been genetically engineered to produce glycoproteins comprising one or more human-like complex or human-like hybrid N-glycans such as GlcNAcMan3GlcNAc2.

As used herein, the term "myeloid cytopenia" refers to a hematological disorder characterized by an abnormally low number of myeloid cells. As used herein, the term includes neutropenia and monocytopenia and excludes thrombocytopenia and erythropenia.

As used herein, the term "monocytopenia" refers to a hematological disorder characterized by an abnormally low number of monocytes.

As used herein, the term "neutropenia" refers to a hematological disorder characterized by an abnormally low number of neutrophils, for example under 1500 neutrophils/µL of blood, preferably under 1000 neutrophils/µL of blood, and most preferably under 500 neutrophils/µL of blood.

As used herein, this term includes chronic, cyclic and acute neutropenia. The neutropenia may for example correspond to a chronic idiopathic neutropenia, a congenital neutropenia or a secondary neutropenia such as an infection-induced neutropenia, a drug-induced neutropenia, an alcoholism-induced neutropenia, an autoimmune neutropenia, a chronic secondary neutropenia in AIDS, a neutropenia caused by bone marrow replacement, a neutropenia caused by cytotoxic chemotherapy, a neutropenia caused by radiation therapy, a neutropenia caused by folate or vitamin B12 deficiency, a neutropenia caused by hypersplenism, or a neutropenia caused by T γ-lymphoproliferative disease.

By "patient in need thereof" is meant an individual suffering from or susceptible of suffering from a myeloid cytopenia or related complications to be treated. The individuals to be treated in the frame of the invention are preferably human beings.

In one particular embodiment, the patient in need thereof is a patient undergoing hematopoietic stem cell transplantation (HSCT).

As used herein, the term "patient undergoing hematopoietic stem cell transplantation" (or HSCT) refers to a human being which has to be transplanted with HSC graft. Typically, said patient is affected with a disorder which can be cured by HSCT.

In one embodiment, the patient undergoing HSCT is affected with a disorder selected from the group consisting of leukemia, lymphoma, myeloproliferative disorders, myelodysplastic syndrome (MDS), bone marrow (BM) failure syndromes, congenital immunodeficiencies, enzyme deficiencies and hemoglobinopathies.

As used herein, the terms "hematopoietic stem cell transplantation" or "HSCT" refer to a component of the treatment of a wide array of hematologic disorders. Generally, there are two types of HSCTs: autologous and allogeneic transplantation.

In one embodiment, the HSCT is an allogeneic HSCT. As used herein, the term "allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor. Allogeneic transplantation involves infusion of donor stem cells, typically using a donor that matches the recipient's MHC. However, matched unrelated donor (MUD) transplants are also associated with a stronger graft versus host reaction, and thus result in higher mortality rates.

In another embodiment, the HSCT is an autologous HSCT. As used herein, the term "autologous" refers to deriving from or originating in the same subject or patient. An "autologous transplant" refers to collection and retransplant of a subject's own cells or organs. Autologous transplantation involves infusion of a recipient's own cells following myeloablative treatment. Autologous cell transplants minimize the risk of graft versus host disease (GVHD) and result in reduced complications.

As used herein, the term "myeloablative" or "myeloablation" refers to impairment or destruction of the hematopoietic system, typically by exposure to a cytotoxic agent or radiation. Myeloablation encompasses complete myeloablation brought on by high doses of cytotoxic agent or total body irradiation that destroys the hematopoietic system. It also includes a less than complete myeloablated state caused by non-myeloablative conditioning (myelosuppressive treatment). Thus, a non-myeloablative conditioning is a treatment that does not completely destroy the subject's hematopoietic system.

In one embodiment, the complications related to myeloid cytopenia are viral, bacterial and/or fungal infections.

Non-limiting examples of viral infections include Herpes simplex virus (HSV) infections, Cytomegalovirus (CMV) infections, Varicella-zoster virus (VZV) infections, Human herpes virus 6 (HHV6) infections, Epstein-Barr virus (EBV) infections, respiratory virus infections (such as respiratory syncytial virus (RSV), parainfluenza virus, rhinovirus, and influenza virus) and adenovirus infections.

Non-limiting examples of bacterial infections include Gram-negative bacteria infections such as *Escherichia* (e.g. *Escherichia coli*), *Salmonella*, *Shigella*, and other Enterobacteriaceae, *Pseudomonas* (e.g. *Pseudomonas aeruginosa*), *Moraxella*, *Helicobacter*, and *Legionella* infections.

Non-limiting examples of fungal infections include *Aspergillus* infection (e.g. *Aspergillus fumigatus*), *Candida* infection (e.g. *Candida albicans* and non-*albicans Candida*) and other emerging fungi infections including *Trichosporon*, *Alternaria*, *Fusarium*, and *Mucorales* infections.

In one particular embodiment, said complications are early infections occurring between 0-100 days after HSCT.

In other particular embodiment, said complications are late infections occurring at least 100 days until at least one year after HSCT.

As used herein, the term "preventing" intends characterizing a prophylactic method or process that is aimed at delaying or preventing the onset of a disorder or condition to which such term applies.

As used herein, the term "treating" intends characterizing a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

Alternatively, a nucleic acid encoding a polypeptide of the invention (such as the M-CSF polypeptides as shown in SEQ ID NO: 1 to SEQ ID NO: 5 or a IL-34 polypeptide as shown in SEQ ID NO: 6) or a vector comprising such nucleic acid or a host cell comprising such expression vector may be used in preventing or treating meloid cytopenia and related complications in a patient in need thereof.

Accordingly, another aspect of the invention relates to a nucleic acid encoding an amino acids sequence comprising any one SEQ ID NO: 1 to SEQ ID NO: 6 as described here above for use in preventing or treating meloid cytopenia and related complications in a patient in need thereof.

Nucleic acids of the invention may be produced by any technique known per se in the art, such as, without limitation, any chemical, biological, genetic or enzymatic technique, either alone or in combination(s).

Another aspect of the invention is an expression vector comprising a nucleic acid sequence encoding an amino sequence comprising any one SEQ ID NO: 1 to SEQ ID NO: 6 as described here above for use in preventing or treating meloid cytopenia and related complications in a patient in need thereof.

In its broadest sense, a "vector" is any vehicle capable of facilitating the transfer of a nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the nucleic acid sequences of interest. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N. J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers and microencapsulation.

Another aspect of the invention relates to a host cell comprising an expression vector as described here above for use in preventing or treating myeloid cytopenia and related complications.

According to the invention, examples of host cells that may be used are human monocytes (particularly those obtained from the subject to be treated).

The means by which the vector carrying the gene may be introduced into the cells include, but are not limited to, microinjection, electroporation, transduction, or transfection using DEAE-dextran, lipofection, calcium phosphate or other procedures known to one skilled in the art.

Pharmaceutical Compositions

The invention also relates to comprising a polypeptide as defined herein (or a nucleic acid encoding thereof, an expression vector or a host cell comprising thereof) and one or more pharmaceutically acceptable carriers for use in a method for transiently providing granulocyte/monocyte progenitor cells (GMP) in a patient in need thereof.

The invention further relates to a pharmaceutical composition comprising a polypeptide as defined herein (or a nucleic acid encoding thereof, an expression vector or a host cell comprising thereof) and one or more pharmaceutically acceptable carriers for use in treating myeloid cytopenia and related complications in a patient in need thereof.

Pharmaceutical compositions comprising a polypeptide of the invention include all compositions wherein the polypeptide is contained in an amount effective to achieve the intended purpose. In addition, the pharmaceutical compositions may contain suitable physiologically acceptable carriers comprising excipients and auxiliaries which facilitate processing of the active compounds into preparations which can be used pharmaceutically.

The term "physiologically acceptable carrier" is meant to encompass any carrier, which does not interfere with the effectiveness of the biological activity of the active ingredient and that is not toxic to the host to which is administered. Suitable physiologically acceptable carriers are well known in the art and are described for example in Remington's Pharmaceutical Sciences (Mack Publishing Company, Easton, USA, 1985), which is a standard reference text in this field. For example, for parenteral administration, the above active ingredients may be formulated in unit dosage form for injection in vehicles such as saline, dextrose solution, serum albumin and Ringer's solution.

Besides the physiologically acceptable carrier, the pharmaceutical compositions of the invention can also comprise minor amounts of additives, such as stabilizers, excipients, buffers and preservatives. The pharmaceutical composition of the invention may further comprise at least one additional compound.

In one embodiment, said at least one additional compound is selected from the group consisting of an antiviral compound, an anti-fungal compound, an anti-bacterial compound, a cytokine or a growth factor.

Anti-viral compounds may be those appropriate to the viruses encountered by the patient. Useful antiviral compounds include, by way of example and not limitation, acyclovir, cidofovir, ganciclovir, idoxuridine, penciclovir, valganciclovir, valacyclovir, vidarabine, amantadine, rimantadine, zanamivir, fomivirsen, imiquimod, and ribavirin. Therapeutics directed against retroviruses include, among others, nucleoside reverse transcriptatse inhibitors (e.g., zidovudine, didanosine, stavudine, zalcitabine, lamividudine), non-nucleoside reverse transcriptase inhibitors (e.g., nevirapine, efavirenz, delvirudine), and protease inhibitors (e.g., saquinivir, indinavir, ritonavir, nelfinavir, amprenavir, and lopinavir).

Anti-fungal compounds may be a systemic antifungal agent. One useful antifungal compound of this type is amphotericin B from the family of polyene macrolide antibiotics. Another antifungal compound is flucytosine, a fluorinated pyrimidine. Deamination of flucytosine by the fungus generates 5-flurouracil, an anti-metabolite and DNA synthesis inhibitor. Flucytosine is typically used for infections of cryptococcus and candiadosis. Although used alone, flucytosine is generally used in combination with amphotericin B. Imidazoles and triazoles represent a broad class of azole based antifungal compounds. Exemplary azole antifungals include, among others, ketoconzaole, itracanazole, fluconazole, econazole, voriconazole, and tercanozole.

Anti-bacterial compounds may be antibiotics suitable for the particular bacterial pathogen. These include both wide spectrum antibiotics and more targeted anti-bacterial compounds. Various classes of anti-bacterial compounds are, by way of example and not limitation, quinolones and fluoroquinolones, [beta]-lactam antibiotics, aminoglycosides, tetracycline, macrolides, and various cogeners thereof. Exemplary quinolone compounds include ciprofloxacin, ofloxacin, sparfloxacin, lomefloxacin, and moxifioxacin. Exemplary [beta]-lactam antibiotics include penicillins (e.g., penicillin G, penicillin V), ampicillin, carbenicillin, methicillin, carbapenem, and cephalosporins (e.g., cephalothin, cefamandole, cefaclor, cefonicid, cefotetan, cefatoxime, ceftazidime, ceftizoxime, cefepime). Exemplary aminoglycosides include neomycin, streptomycin, kanamycin, gentamicin, tobramycin, amikacin, and netilmicin. Exemplary macrolides include erythromycin, clarithromycin, and azithromycin.

The polypeptides of the invention may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use. Parenteral and topical routes are particularly preferred.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

The doses used for the administration can be adapted as a function of various parameters, and in particular as a function of the mode of administration used, of the relevant pathology, or alternatively of the desired duration of treatment. For example, it is well within the skill of the art to start doses of the compounds at levels lower than those required to achieve the desired therapeutic effect and to gradually increase the dosage until the desired effect is achieved. However, the daily dosage of the polypeptides may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day.

In another aspect, the invention relates to a method for transiently providing GMP cells to a patient in need thereof, comprising a step of administering to said patient a therapeutically effective amount of a M-CSF polypeptide or an agonist of the M-CSF receptor.

In still another aspect, the invention relates to a method for preventing or treating myeloid cytopenia and related complications in a patient in need thereof, comprising a step of administering to said patient a therapeutically effective amount of a M-CSF polypeptide or an agonist of the M-CSF receptor.

By "therapeutically effective amount" is meant an amount sufficient to achieve a concentration of polypeptide which is capable of preventing, treating or slowing down the disease to be treated. Such concentrations can be routinely determined by those of skilled in the art. The amount of the polypeptide actually administered will typically be determined by a physician or a veterinarian, in the light of the relevant circumstances, including the condition to be treated, the chosen route of administration, the actual compound administered, the age, weight, and response of the subject, the severity of the subject's symptoms, and the like. It will also be appreciated by those of skilled in the art that the dosage may be dependent on the stability of the administered polypeptide.

In a particular embodiment, the invention relates to a method for transiently providing GMP cells to a in a patient undergoing HSC transplantation, comprising a step of administering to said patient a therapeutically effective amount of a M-CSF polypeptide or an agonist of the M-CSF receptor simultaneously and/or subsequently to the HSCT.

In still another aspect, the invention further relates to a method for preventing or treating myeloid cytopenia and related complications in a patient undergoing HSC transplantation, comprising a step of administering to said patient a therapeutically effective amount of a M-CSF polypeptide or an agonist of the M-CSF receptor simultaneously and/or subsequently to the HSCT.

As used herein, the term "simultaneously" means that the polypeptide of interest is administered to the recipient patient the same day that the hematopoietic stem cell transplantation (HSCT).

As used herein, the term "subsequently" means that the polypeptide of interest is administered to the recipient patient after HSCT, for instance 2, 3, 4, 5, 6 or 7 days following HSCT.

In one embodiment, the treatment with a M-CSF polypeptide or an agonist of the M-CSF receptor is administered in more than one cycle, i.e. the administration of a M-CSF polypeptide or an agonist of the M-CSF, is repeated at least once.

For example, 2 to 10 cycles or even more, depending on the specific patient status and response, may be administered. The intervals, i.e. the time between the start of two subsequent cycles, are typically several days.

In another aspect, the invention further relates to a hematopoietic stem cell graft primed in the presence of a M-CSF polypeptide or an agonist of the M-CSF receptor.

Ex vivo treatment with a M-CSF polypeptide or an agonist of the M-CSF receptor improves myeloid rescue of the patient following myeloablative or myelosuppressive cytoreductive therapy regimens in order to prevent or treat meloid cytopenia and related complications in a patient in a patient undergoing HSCT.

As used herein, the term "hematopoietic stem cell graft" refers to an optimal number of hematopoietic stem cells/kg patient in order to achieve a successful stem cell transplantation. The hematopoietic stem cell graft can vary widely as a function of the age, weight and state of health of the patient, the nature and the severity of the indication. Suitable dosage ranges for the HSCs vary according to these considerations.

There are three main sources of hematopoietic stem cells (HSC) useful as hematopoietic stem cell graft: bone marrow (BM), peripheral blood, and umbilical cord blood. Umbilical cord blood (UCB) is a practical alternative source to other hematopoietic progenitor sources (e.g., bone marrow and mobilized peripheral blood) for related and unrelated allogeneic hematopoietic stem cell transplantation.

As used herein, the terms "hematopoietic stem cell" or "HSC" refer to clonogenic, self renewing multipotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers. The marker phenotypes useful for identifying HSCs are those commonly known in the art. For human HSCs, the cell marker phenotypes preferably include CD34$^+$ CD90(ThyI)$^+$ Lin$^-$. Human HSCs may be further characterized as AC133 positive; CD38 negative/low; and negative for the specific lineage markers CD2, CD3, CD19, CD16, CD14, CD15, and Glycophorin A. Usually the cell populations used in the invention are at least about 50% of the cells present having the hematopoietic stem cell phenotype, more usually at least about 75% of the cells present, preferably at least about 85% of the cells present, and may be as high as about 95% of the cells present.

"Marker phenotyping" refers to identification of markers or antigens on cells for determining its phenotype (e.g., differentiation state and/or cell type). This may be done by immunophenotyping, which uses antibodies that recognize antigens present on a cell. The antibodies may be monoclonal or polyclonal, but are generally chosen to have minimal crossreactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

In one embodiment, the hematopoietic stem cell graft is selected from the group consisting of a mobilized peripheral blood sample or a bone marrow (BM) obtained from a donor (allogeneic or autologous graft), or an umbilical cord blood (UCB) sample.

As used herein, the term "primed" graft refers to a graft that that have been activated or changed to express certain genes in order to specifically and transiently provide increased granulocyte/monocyte progenitor cells (GMP) without compromising stem cell activity. Priming of hematopoietic progenitor cells graft obtained from peripheral blood, bone marrow, or umbilical cord blood further allows for reducing the risk of infection to the patient.

Priming may occur by incubating the cells for a period of at least 1 hr, preferably from 1 hr to two weeks; from 1 to 10 days, from 5 to 10 days or 5 to 7 days, with the M-CSF polypeptide or the agonist of the M-CSF receptor as described above, and then optionally separating the cytokine from the cells and infusing the primed cells into the recipient patient.

The M-CSF polypeptide or the agonist of the M-CSF receptor of the invention may be present in the incubation mix in an amount of at least about 1 ng/ml, from about 1 to 1000 ng/ml, from about 10 to 500 ng/ml, from about 20 to 250 ng/ml.

In another aspect, the invention relates to a hematopoietic stem cell graft primed in the presence of a M-CSF polypeptide or an agonist of the M-CSF receptor for use in preventing or treating myeloid cytopenia and related complications in a patient undergoing HSCT.

The invention further relates to a method for preventing or treating myeloid cytopenia and related complications in a patient undergoing HSC transplantation, comprising a step of administering to said patient a therapeutically effective amount of hematopoietic stem cell graft primed in the presence of a M-CSF polypeptide or an agonist of the M-CSF receptor.

Kit-of-Part Compositions

The hematopoietic stem cell graft primed or not and the M-CSF polypeptide or the agonist of the M-CSF receptor may be combined within one formulation and administered simultaneously. However, they may also be administered separately, using separate compositions. It is further noted that they may be administered at different times.

Thus, in another aspect, the invention relates to a kit-of-part composition comprising (i) a hematopoietic stem cell graft and (ii) a M-CSF polypeptide or an agonist of the M-CSF receptor for simultaneous and/or subsequently use in preventing or treating myeloid cytopenia and related complications in a patient undergoing HSCT.

In one embodiment, the kit may also comprise at least one additional compound is selected from the group consisting of an antiviral compound, an anti-fungal compound, an anti-bacterial compound, a cytokine or a growth factor.

Examples of antiviral compounds, anti-fungal compounds, and anti-bacterial compounds useful have been described above.

The terms "kit", "product" or "combined preparation", as used herein, define especially a "kit of parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes. When the administration is sequential, the first partner may be for instance administered 1, 2, 3, 4, 5, 6, 7, days before the second partner.

In another aspect, the invention relates to a method for improving the survival time of a patient undergoing HSCT, comprising a step of administering to said patient a therapeutically effective amount of a M-CSF polypeptide or an agonist of M-CSF receptor simultaneously and/or subsequently to the HSCT.

As used herein, the term "survival" refers to the patient remaining alive, and includes overall survival (OS) as well as progression free survival (PFS).

As used herein, the term "overall survival" refers to the patient remaining alive for a defined period of time, such as 3 months, 6 months, 1 year, etc from the time of diagnosis or treatment.

As used herein, the term "progression free survival" refers to the patient remaining alive, without disease progression (such as uncontrolled or untreatable opportunistic infections occurring in transplanted patients).

As used herein, the term "improving the survival time" is meant increasing overall or progression free survival in a treated patient relative to an untreated patient (i.e. relative to a patient not treated with a M-CSF polypeptide or an agonist of the M-CSF receptor).

An improvement in survival time of a population may be measured by any reproducible means. In a preferred aspect, an improvement in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another particular embodiment, the invention relates to a method for improving the survival time of a patient undergoing HSCT, comprising (i) a first step of administering to said patient a therapeutically effective amount of a M-CSF polypeptide or an agonist of the M-CSF receptor before the HSCT, and (ii) a second step of administering to said patient a therapeutically effective amount of a M-CSF polypeptide or an agonist of M-CSF receptor simultaneously and/or subsequently to the HSCT.

In a further aspect, the invention relates to a method for improving the survival time of a patient of a patient undergoing HSCT, comprising a step of administering to said patient a therapeutically effective amount of hematopoietic stem cell graft primed in the presence of a M-CSF polypeptide or an agonist of the M-CSF receptor.

The invention will be further illustrated by the following figures and examples. However, these examples and figures should not be interpreted in any way as limiting the scope of the present invention.

FIGURES

Figure 1:
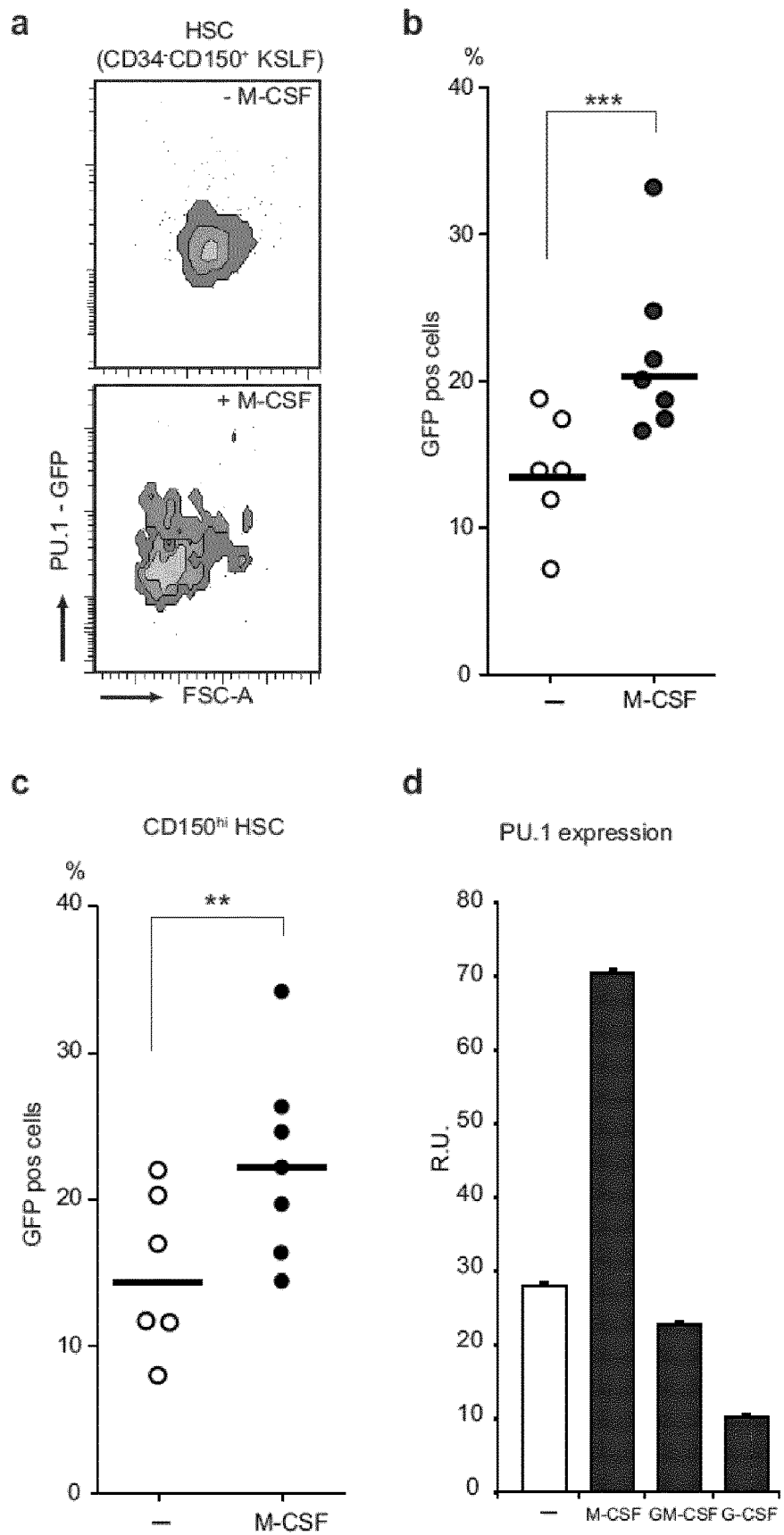

FIG. 1: M-CSF activates the myeloid master regulator PU.1 in HSC.

a-c) Representative FACS profile (a) and quantification of GFP expression in HSC (b) or CD150$^{hi}$HSC (c) of PU.1-GFP reporter mice 16 h after control (PBS) or M-CSF injection. *p=0.009; p=0.03.

d) Quantitative RT-PCR analysis of PU.1 expression normalized to GAPDH expression (R.U.) in sorted HSC after 16 h culture in the absence or presence of M-CSF, GM-CSF or G-CSF. Error bars show standard deviation of duplicates.

Figure 2:
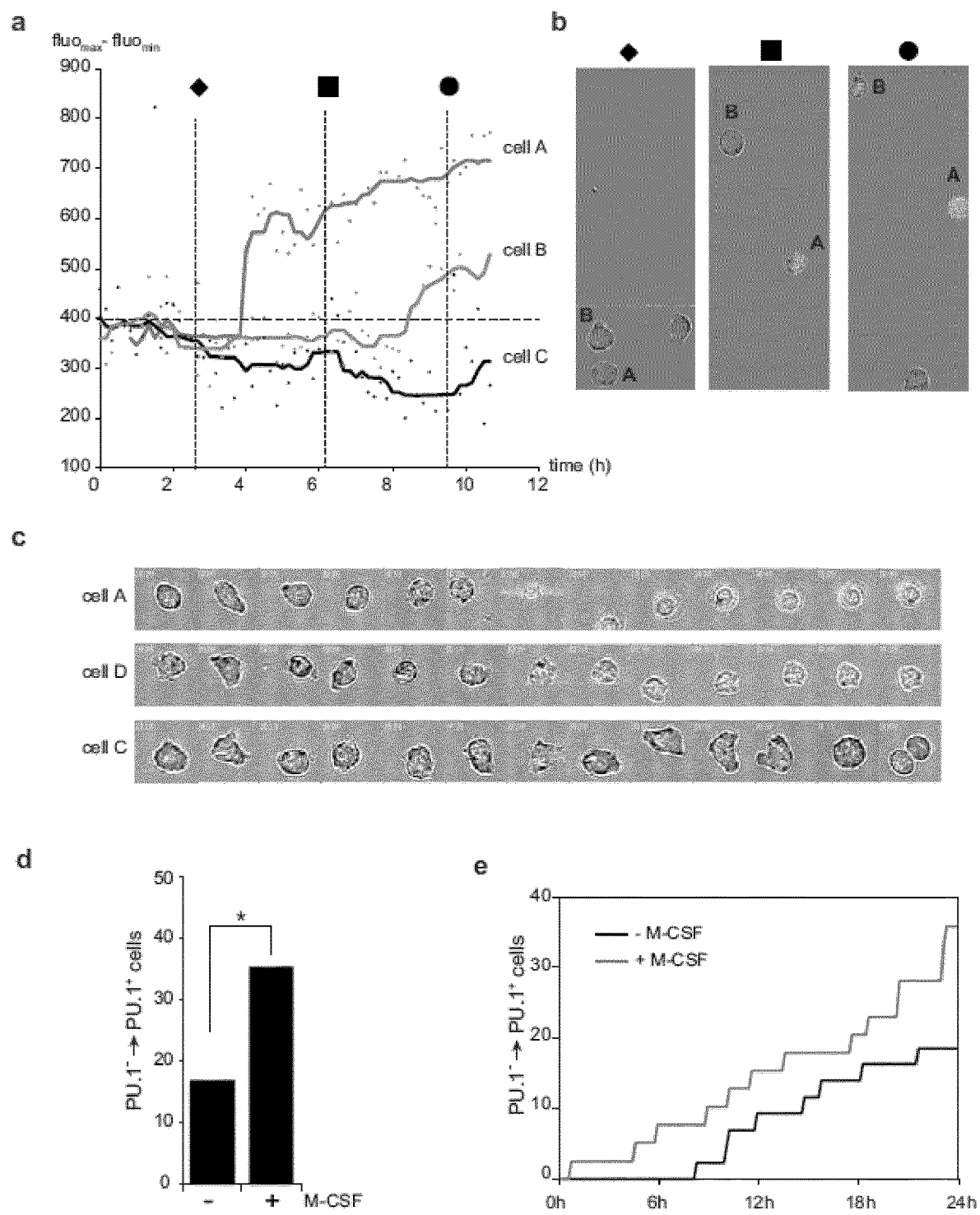

FIG. 2: Continuous video-imaging of PU.1+ cell generation from individual PU.1 negative HSC.

a) GFP-fluorescence intensity at 10 minute intervals (dots) and sliding median (lines) over 12 h observation time of 3 individual GFP negative sorted HSC from PU.1-GFP reporter mice after 18 h in M-CSF culture, representative of cells quantified in FIG. 2e (n=39). Green: cells activating GFP, black: cell remaining GFP negative.

b) Still photos taken at times indicated by symbols in a) of fields with 2 representative HSC (cells A,B) showing activation of PU.1 at different time points. Cell C was outside of the shown field.

c) Still photos taken at 40 min intervals over 8 h of 3 representative HSC in M-CSF culture without (cell C) or with activation of PU.1 (cells A,D), representative of cells quantified in FIG. 2e (n=39).

d) Quantification of PU.1+ cells derived from PU.1 negative HSC (committed cells) with (n=39) or without M-CSF (n=42) as percentage of total cells after 24 h observation period. *p<0.1.

e) Timing of PU.1 activation in PU.1 negative HSC of cells shown in d) over 24 h observation period.

Figure 3:
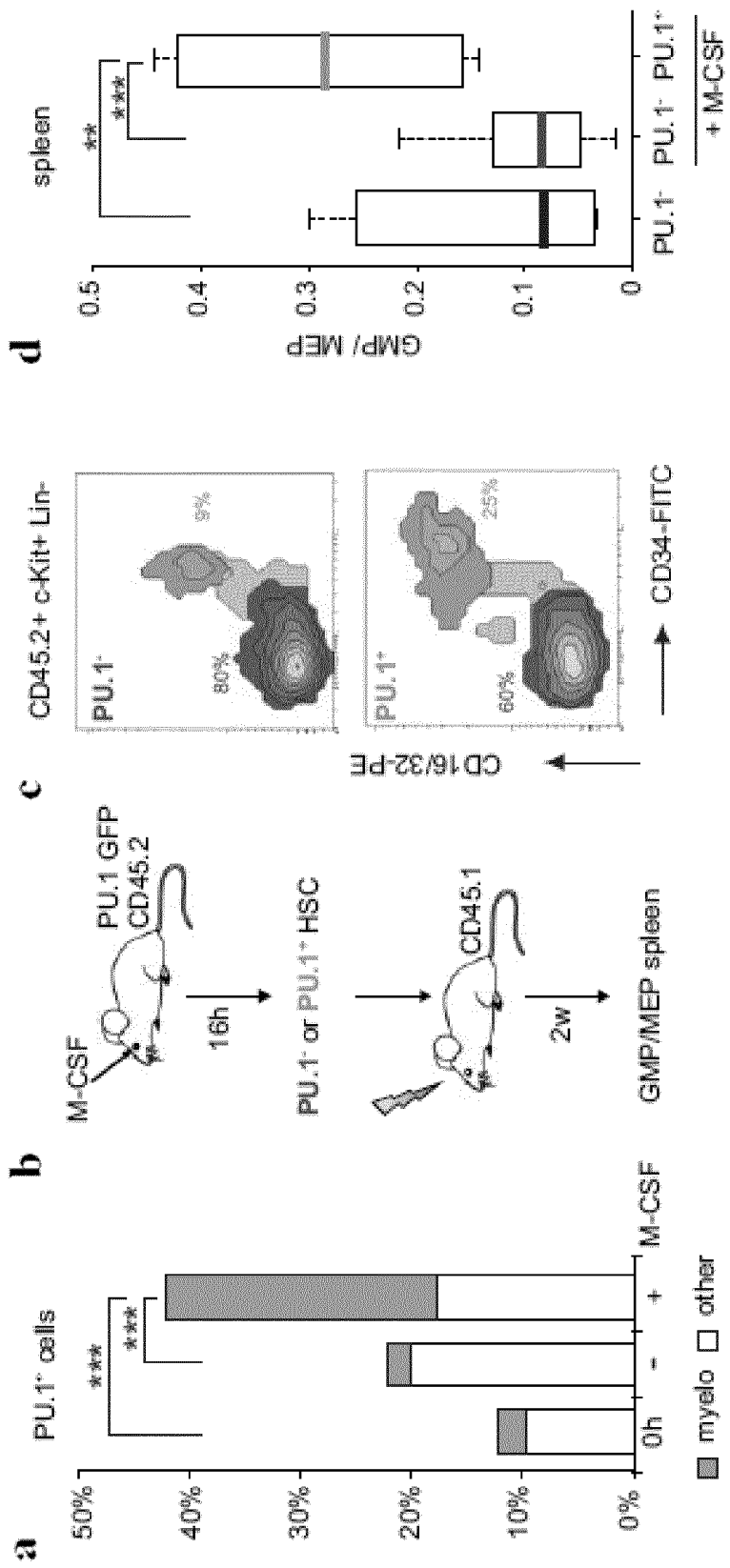

FIG. 3: M-CSF activates PU.1 and instructs myeloid identity in single HSC.

a) Individual PU.1+ cells with a myeloid gene expression profile (blue) or expressing other lineage genes (white) as a percentage of total cells. *** p=0.009 (0 h), and 0.005 (-M-CSF).

b) Experimental design for transplantation of sorted PU.1− and PU.1+ HSC from in vivo M-CSF primed CD45.2 PU.1-GFP mice into sub-lethally irradiated CD45.1 recipients and analysis of progeny cells after 2 weeks in the spleen.

c,d) Representative FACS profiles (c) and quantification of the ratio (d) of donor GMP and MEP progenitors derived from transplanted PU.1− or PU.1+ HSC before or after M-CSF stimulation in vivo. p=0.05, *p=0.01, n=4, 8, 4.

Figure 4:
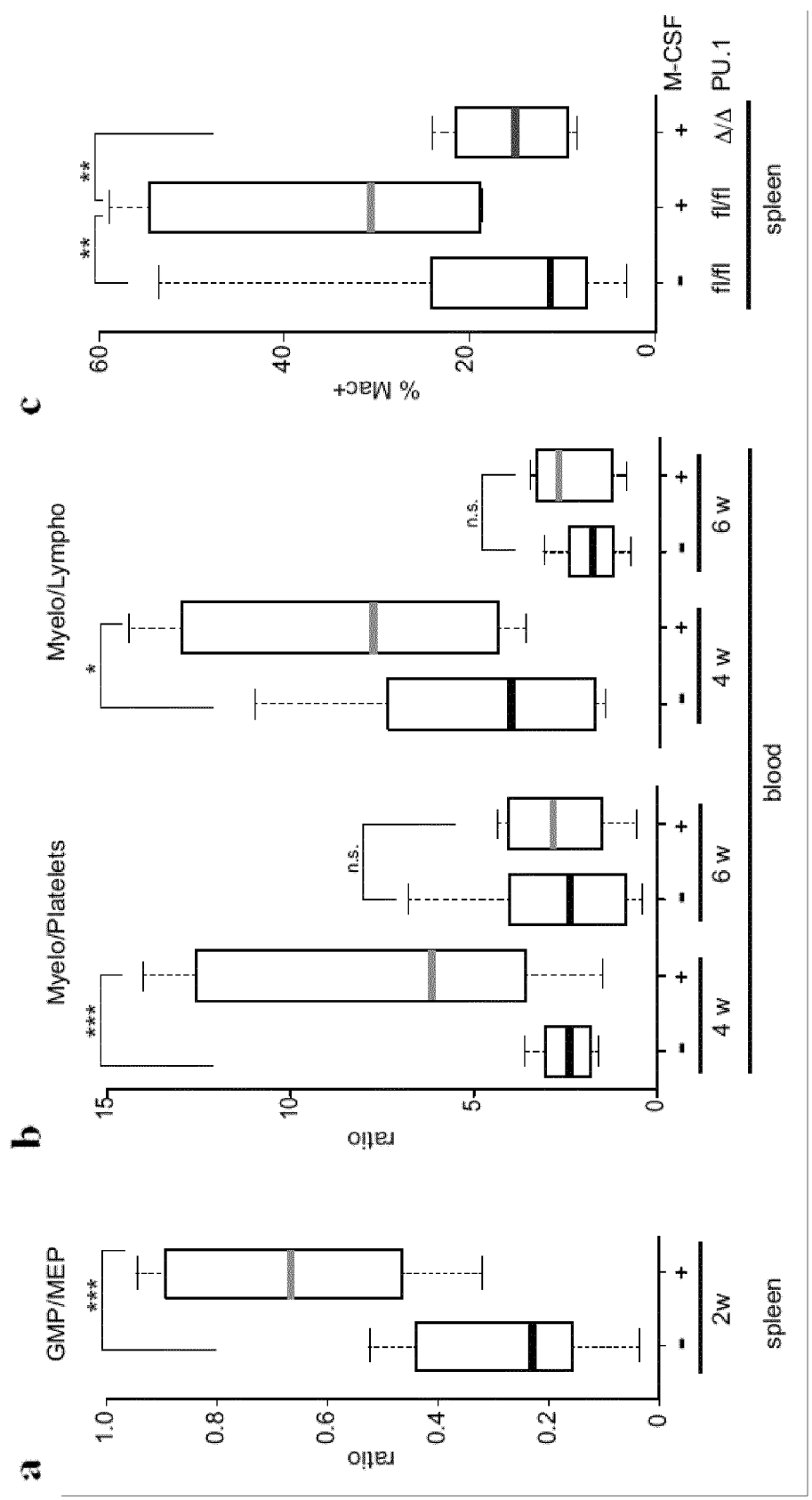
Figure 6:
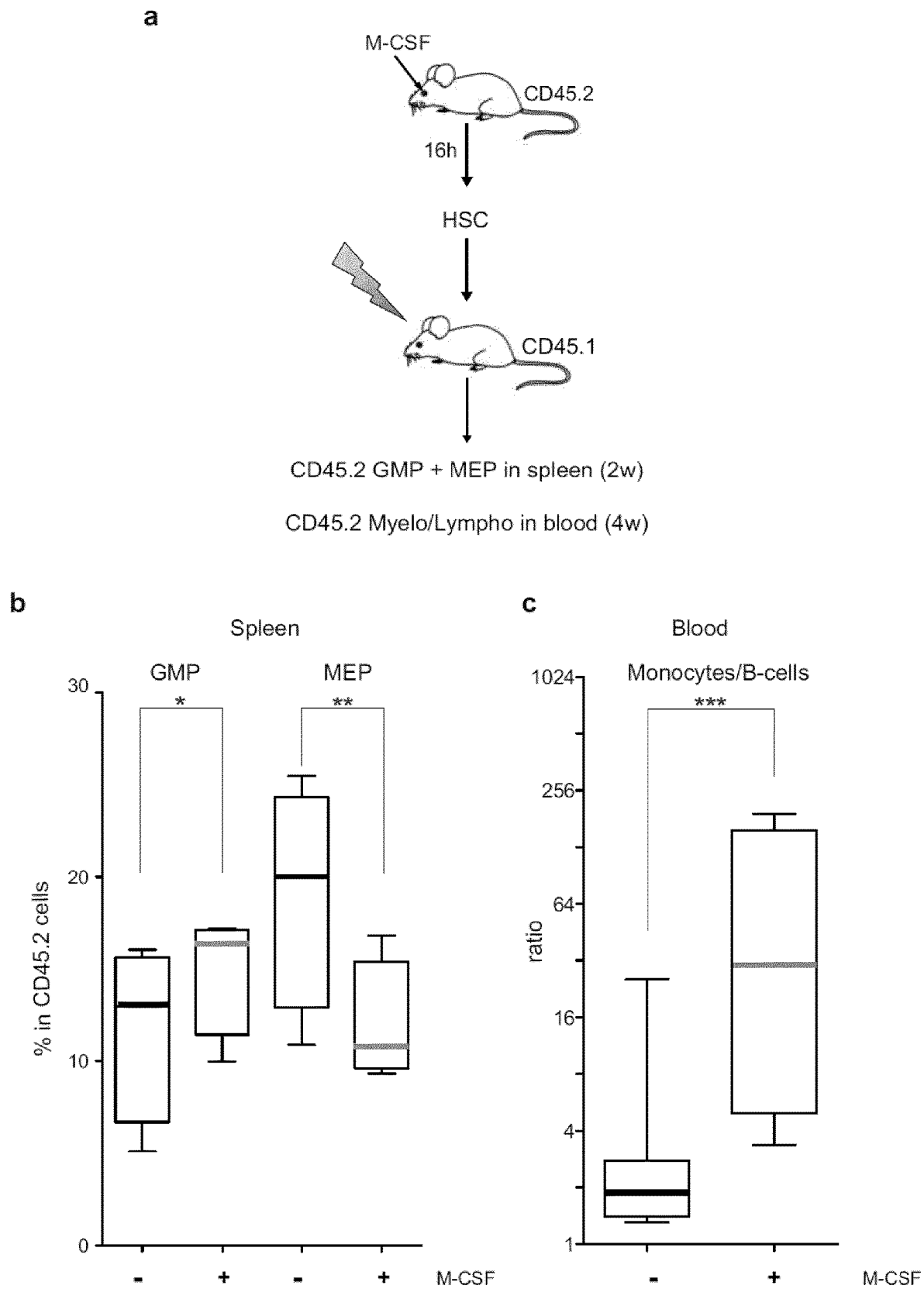

FIG. 4: M-CSF stimulates a reversible, PU.1-dependent myeloid differentiation preference in single HSC in vivo.

a) Ratio of donor GMP to MEP progenitors in the spleens of sub-lethally irradiated recipients 2 weeks after transplantation of in vivo M-CSF primed or control HSC. Experimental design is shown in FIG. 6. ***p=0.003, n=8, 9.

b) Donor contribution to blood of competitively reconstituted mice 4 weeks and 6 weeks after transplantation of M-CSF primed or control HSC, expressed as ratio of CD11b+ myeloid cells to platelets or CD19+ lymphoid cells. ***p=0.01, n=10.6, *p=0.07, n=6, 4.

c) Donor contribution to Mac+ myeloid cells in the spleen of sub-lethally irradiated recipients 2 weeks after transplantation of control or M-CSF primed HSC with control (fl/fl) or deleted (Δ/Δ) PU.1 alleles. **p=0.05, n=6, 4, 5.

Figure 5:
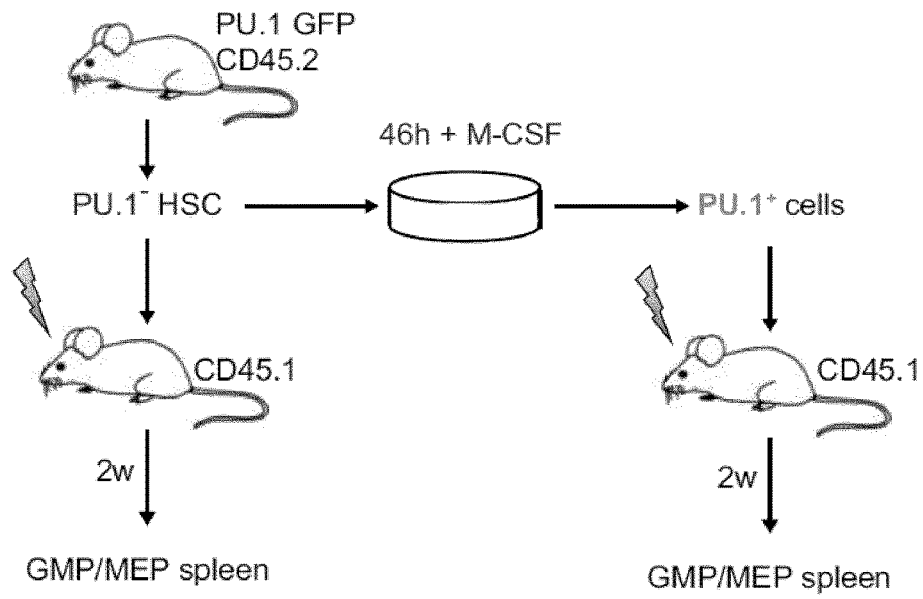
Figure 5:
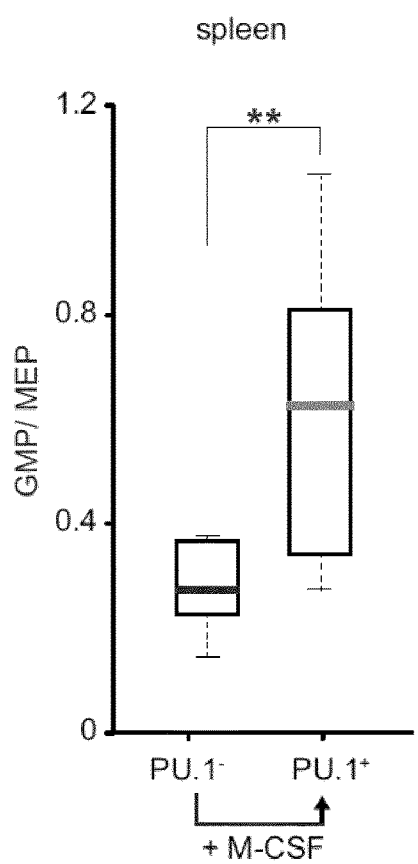
Figure 5:
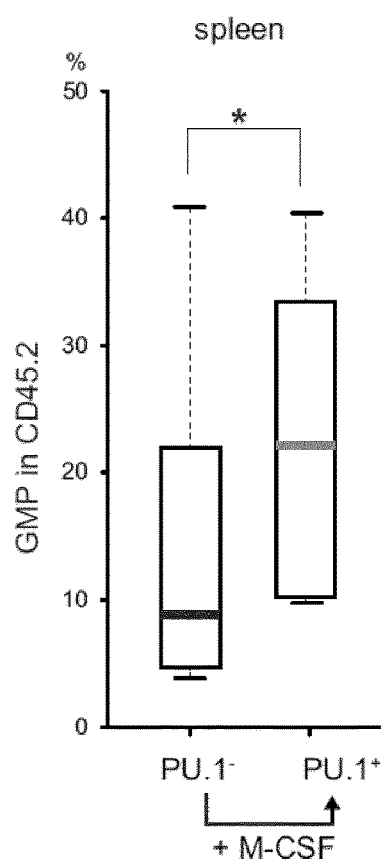

FIG. 5: Differentiation potential of M-CSF induced PU.1+ cells.

a) Experimental design for transplantation of sorted CD45.2 PU.1− HSC before and after induction of PU.1+ cells in M-CSF culture into sub-lethally irradiated CD45.1 recipients and analysis of progeny cells after 2 weeks in the spleen.

b,c) Quantification of the ratio of donor GMP to MEP progenitors (b) and total GMP (c) derived from transplanted PU.1− HSC before or PU.1+ cells after M-CSF culture. **p=0.02, *p=0.07, n=6, 7.

FIG. 6: Differentiation potential of M-CSF primed HSC.

a) Experimental design for transplantation of in vivo M-CSF primed CD45.2 HSC into sub-lethally irradiated CD45.1 recipients and analysis of progeny cells after 2 weeks in the spleen or 4 weeks in the blood.

b) Percentage of GMP and MEP progenitors in total donor cells derived from control (PBS) or M-CSF primed HSC in the spleen 2 weeks after transplantation.
*p=0.1, **p=0.04, n=4, 4 c) Quantification of the ratio of donor CD11b+ SSClo monocytes to CD19+ B-cells in the blood 4 weeks after transplantation. ***p=0.009, n=8, 4.

FIG. 7: Competitive transplantation of M-CSF primed HSC a) Experimental design for competitive transplantation of FACS sorted in vivo M-CSF primed HSC (CD150+CD34−CD135-KSL) from actin-GFP CD45.2 mice together with CD45.2 competitor HSC into lethally irradiated CD45.1 recipients and analysis of blood cell contribution.

b) Gating strategy for quantification of actin-GFP+ HSC derived platelets, lymphoid and myeloid blood cells.

c) Donor contribution to blood of competitively reconstituted mice 4, 6 and 14 weeks after transplantation of M-CSF primed or control HSC, expressed as percentage of GFP+ donor cells in Mac+ myeloid, CD19+ B Cells, CD61+ Platelets (4, 6 and 14 weeks) and CD3e T Cells (14 weeks) and normalized to total GFP contribution in CD45.2 donor compartment. ** p=0.03, n=6, 4.

Figure 8:
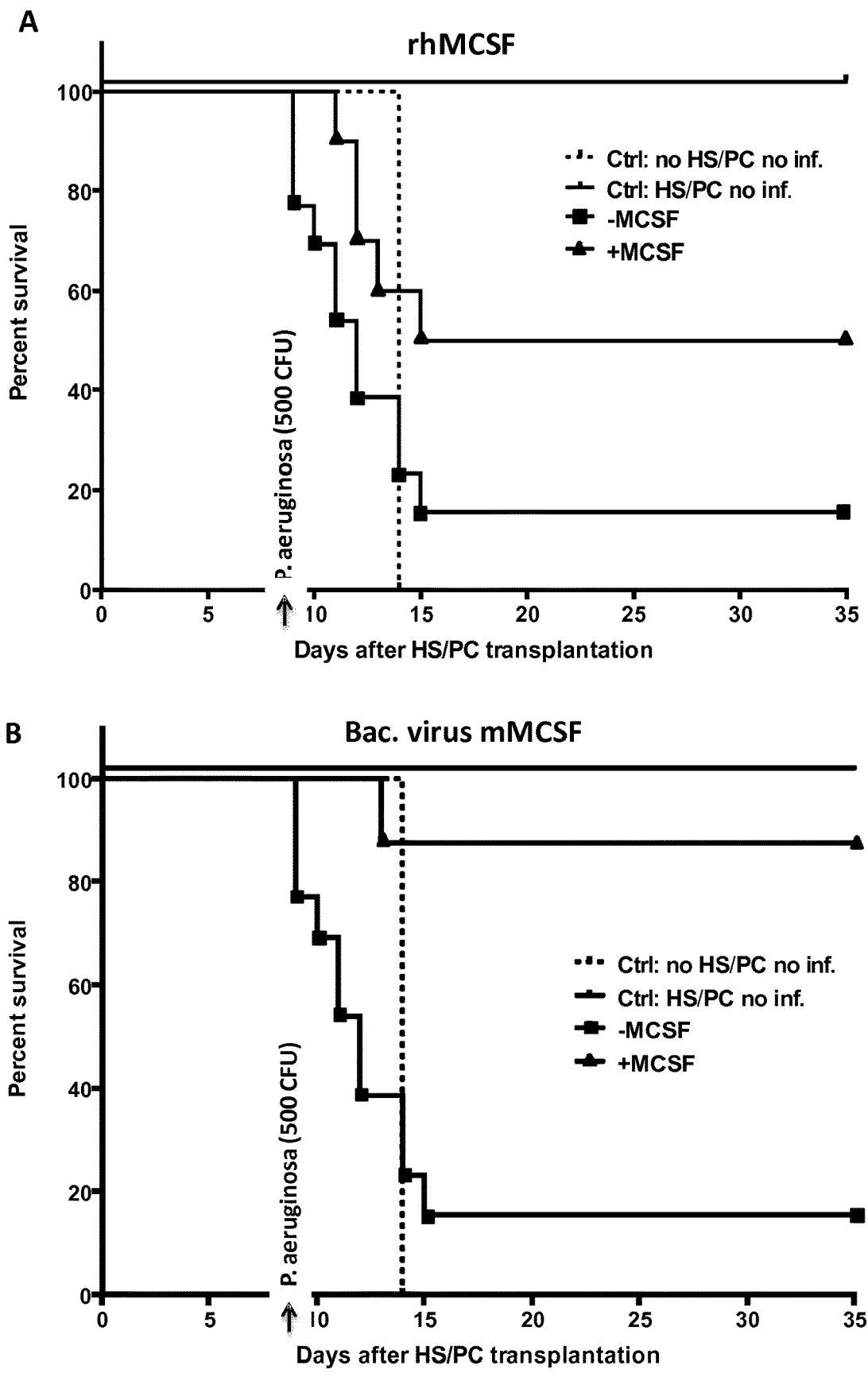

FIG. 8: MCSF stimulation following Hematopoietic Stem and Progenitor Cells (HS/PC) transplantation protects against *Pseudomonas aeruginosa* infection (p<0.01).

a) rhMCSF treatment
b) Bac. virus mMCSF treatment

Figure 9:
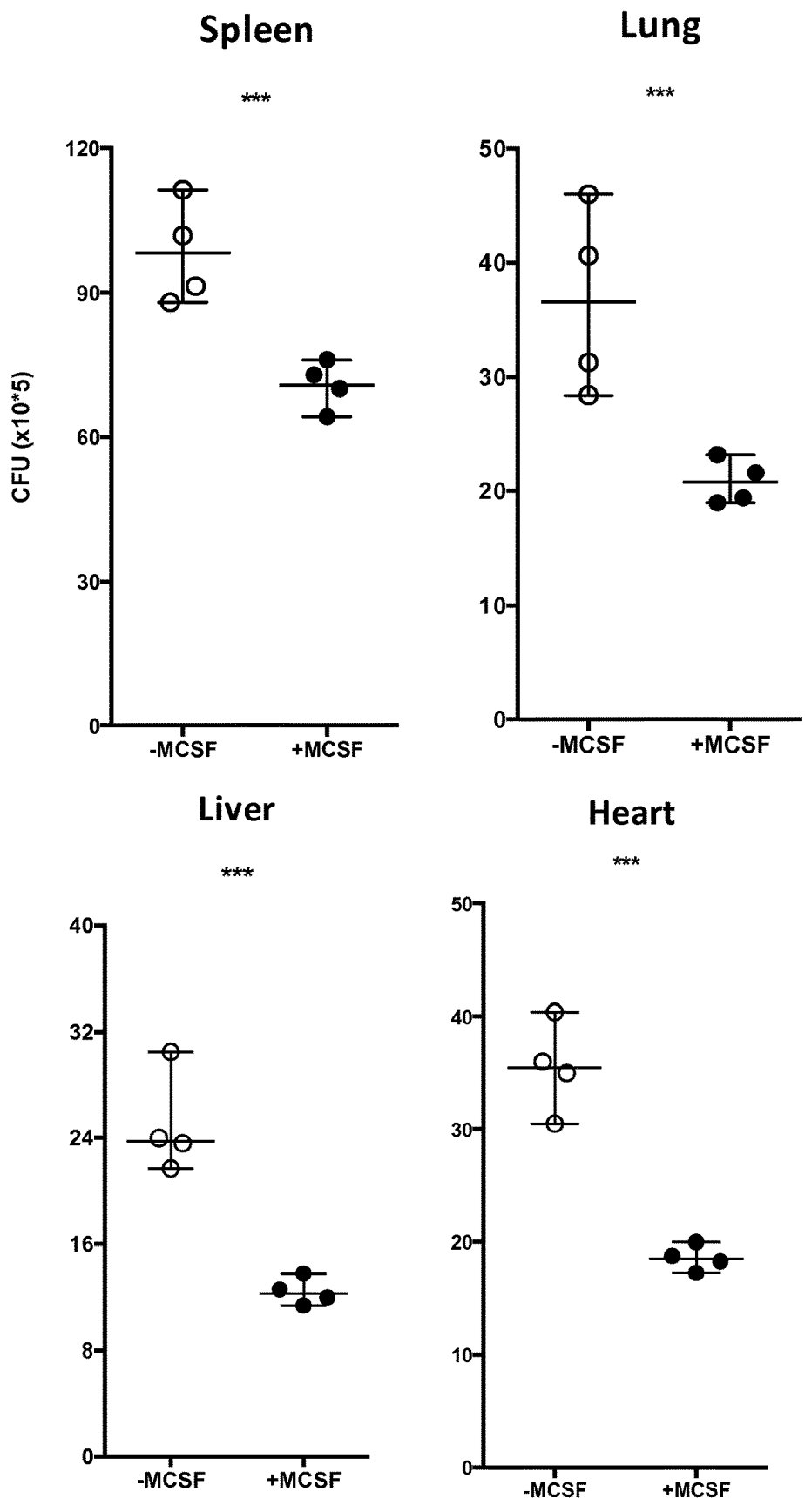

FIG. 9: MCSF stimulation after HS/PC transplantation reduced bacterial tissue load (***P<0.01).

Figure 10:
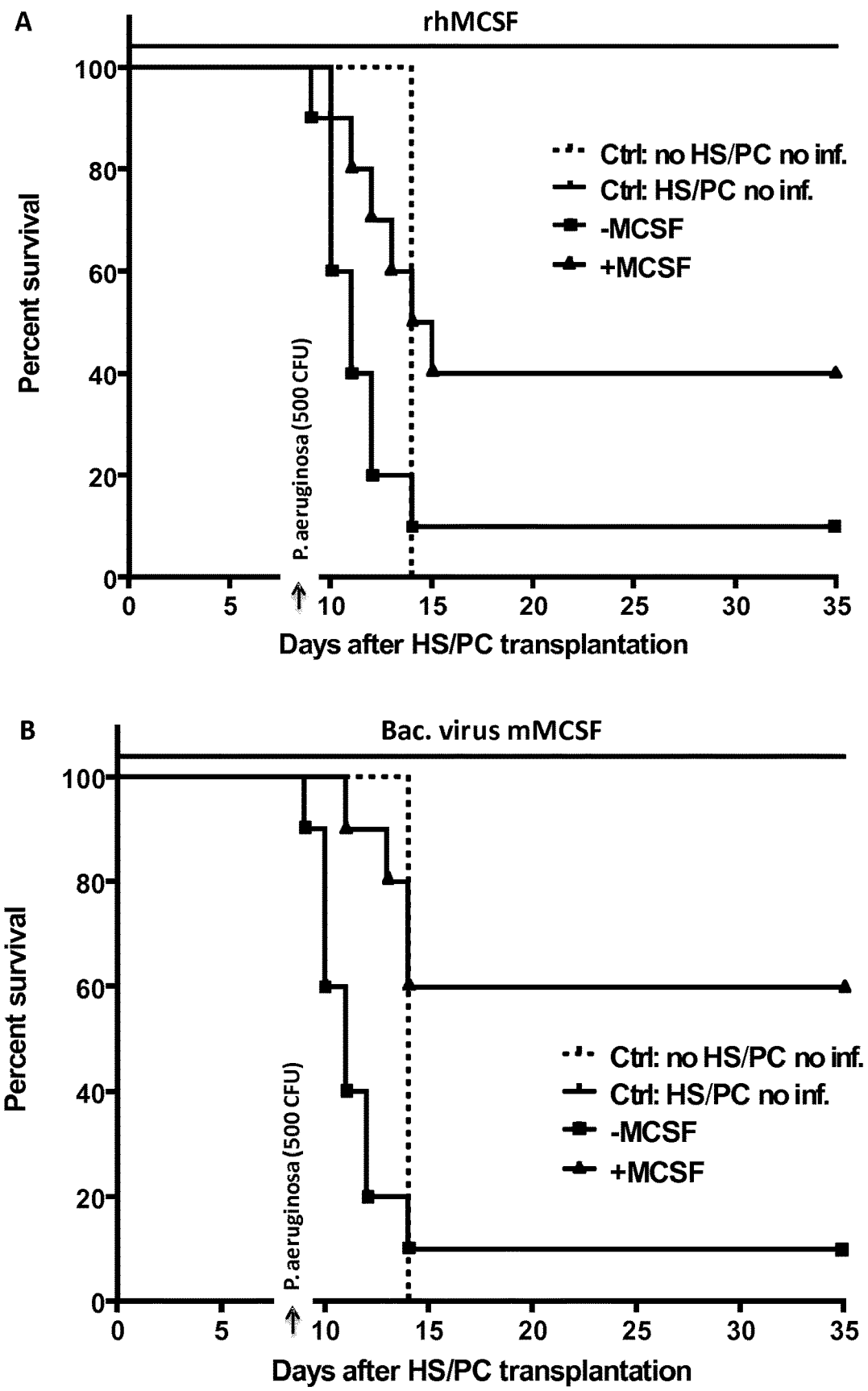

FIG. 10: MCSF stimulation following HS/PC transplantation protects against *Aspergillus fumigatus* infection (p<0.01).

a) rhMCSF treatment
b) Bac. virus mMCSF treatment

EXAMPLE 1

M-CSF Instructs Myeloid Lineage Fate in Single Haemotopoietic Stem Cells

Material & Methods
Methods Summary:

Flowcytometry, bone marrow transplantation and in vivo immunofluorescence of HSC were performed essentially as described[3]. Single cell nano-fluidics-based real-time PCR was performed using a BIOMARK™ HD system and 48.48 dynamic arrays (FLUIDIGM, CA, USA) and videomicroscopy analysis followed proposed standards[24]. Details of procedures and reagents are described in Supplementary Methods.

Mice:

CD45.1 and C57Bl/6 mice were obtained from Charles River. PU.1-GFP[31] M-CSFR$^{-/-}$[27] and PU.1$^{fl/fl}$ [32] mice have been described. Age- and sex-matched CD45.1 recipients that were reconstituted as described[3] with CD45.2 foetal liver from wt or M-CSFR$^{-/-}$ embryos[27] and PU.1$^{fl/fl}$ or PU.1$^{fl/fl}$::MxCre bone marrow, were used to isolate CD150+ CD34− KSLF HSC not earlier than 8 weeks after reconstitution. For in vivo injections the 10 μg/mouse M-CSF, 5 mg/kg LPS (055:B5 *E. coli*) or sorted cells were injected in 100 μl of PBS into the retro-orbital sinus. For HSC transplantation 400 CD150+CD34− KSLF HSC were sorted from CD45.2 mice and mixed with 100.000 Lin$^+$ Sca$^-$ CD45.1 carrier cells prior to injection into sub-lethally irradiated (4.5 Gy) CD45.1 recipient mice. For competitive transplantations, 1300 CD150+, CD34-KSLF HSC were isolated 16 h after control or 10 μg M-CSF injection from actin-GFP CD45.2 mice[33], mixed with equal numbers of CD45.2 competitor HSC and injected with 300.000 Lin$^+$ Sca$^-$ RC-lysed CD45.1 carrier cells into sub-lethally irradiated (4.5 Gy) CD45.1 recipients. Contribution to platelets, CD19+ B-cells and CD11b+ myeloid cells was analysed after 4 and 6 weeks in the blood from mice with at least 5% GFP+ donor cells. For PU.1 deletion PU.1$^{fl/fl}$ or PU.1$^{fl/fl}$::MxCre reconstituted mice were intra-peritoneally injected with 5 μg/g Polyinosinic:polycytidylic acid 7 and 9 days prior to control (PBS) or 10 μg M-CSF injection. All mouse experiments were performed under specific pathogen-free conditions in accordance with institutional guidelines.

FACS Analysis:

For FACS sorting and analysis we used described staining protocols[3] and published stem and progenitor cell definitions[34], FACSCANTO™ BD™ LSRII and FACSARIA™ III equipment and DIVA™ software (BECTON-DICKINSON), analysing only populations with at least 200 events. For HSC analysis we used antibodies anti-CD34-FITC (clone RAM34, BD BIOSCIENCES), anti-CD135-PE (clone A2F10.1, BD BIOSCIENCES), anti-CD150-Pe-Cy7 (clone TC15-12F12.2, BIOLEGEND), anti-CD117-APC H7 (clone 2B8, BD BIOSCIENCES), anti-Sca-1-Pe-Cy5 (clone D7, BIOLEGEND), anti-CD48-APC (clone HM48-1, BIOLEGEND). Diverging from this or in addition we used antibodies anti-CD34 Alexa 700 (clone RAM34, BD BIO- SCIENCES), anti-CD16/32 PE (clone 2.4G2, BD BIOSCIENCES), anti-CD11b PE-CF594 (clone M1/70, BD BIOSCIENCES), anti-CD19PE-Cy7 (clone 1D3, BD biosciences), anti CD45.2 APC (clone 104, BD BIOSCIENCES) and anti CD45.1 Pacific Blue (clone A20, BD BIOSCIENCES) for progenitor and blood cell analysis. LIVE/DEAD Fixable Violet Dead cell dye (Invitrogen) was used as viability marker.

Intra-Splenic Injection of Sorted HSC and Fluorescence Microscopy:

For analysis of HSC in vivo, 1500 to 7000 FACS sorted CD150$^+$ CD34$^-$ KSLF HSC were stained 10 min at 37° C. with 3 µM CFSE (Invitrogen) in PBS/0.5% BSA, washed 3× in PBS/0.5% BSA and injected in 30 µl PBS (containing or not 1 µg of isotype control or AFS98 α-M-CSFR antibody[26] or 2 µM GW2580, 10 µM Ly29400, 10 µM PD98059 or 2 µM SU6656 inhibitors in 0.9% DMSO) into the spleen of anesthetized mice. After 24 h spleens were embedded in OCT (Tissue-Tek, Sakura) and frozen at −80° C. Cryostat sections (5 µm) were prepared from the entire organ, dried and fixed 10 min in 4% PFA/PBS at room temperature (RT) and every 10$^{th}$ section was further processed. After washes in PBS, slides were blocked for 1 hour at RT in PBS/2% BSA/1% Donkey serum/1% FCS/0.1% saponin, incubated for 36 h at 4° C. with anti-PU.1 polyclonal antibody (Santa Cruz) in PBS/0.05% saponin (1:50), washed and incubated with secondary Alexa 546-donkey-anti-rabbit antibody (Molecular probes) in PBS/0.05% saponin (1:500). All immunofluorescence samples were mounted with ProLong Gold DAPI antifade (Molecular probes) and analyzed by multifluorescent microscopy on a Zeiss Axioplan 2. All CFSE+ cells were analysed for PU.1 expression up to ≥30 or ≥50 cells as indicated. Cell counts and staining were verified by a second trained microscopist blinded to sample identity. High-resolution photographs were obtained by confocal microscopy on a Leica SP5X.

In Vitro Culture of HSC:

CD150+CD34− KSLF HSC or CD150+CD34− CD48− KSLF HSC (single cells) were sorted into S-clone SF-03 medium (Sanko Jyunyaku) with 10% FBS supplemented with 100 U/ml penicillin and 100 mg/ml streptomycin (both Invitrogen) and cultivated in uncoated U-Shape 96 well plates (Greiner) in 100 µl SCM, 20 ng/ml rSCF, 50 ng/ml rTPO+/−100 ng/ml rM-CSF or 100 ng/ml rGM-CSF or 100 ng/ml rG-CSF. All cytokines were murine and from PeproTech. Cell viability was analyzed by AnnexinV and Propidium iodide FACS staining[35].

Quantitative Real Time PCR:

Total RNA was isolated and reverse transcribed with µMACS™ ONE-STEP T7 template kit (Miltenyi Biotec) and analysed by quantitative real-time PCR using TAQMAN® Universal PCR Master Mix and a 7500 Fast Real Time PCR System sequence detection system (both Applied Biosystem), following the manufacturers' instructions.

Single Cell Gene Expression Profiling:

Single cells were sorted using the autoclone module on a FACSARIA™ III sorter (Becton-Dickinson) directly into 96 wells plate in the CELLS DIRECT™ Reaction Mix (Invitrogen). Individual cell lysis, cDNA synthesis and amplification was performed according to FLUIDIGM Advanced Development Protocol and single cell microfluidic real time PCR using Dynamic Array IFCs (BIOMARK™ FLUIDIGM) was performed by a trained technician of FLUIDIGM Inc. Preamplified products (22 cycles) were diluted 5-fold prior to analysis with Universal PCR Master Mix and inventoried TAQMAN® gene expression assays (ABI) in 96.96 DYNAMIC ARRAY™ on a BIOMARK™ system (FLUIDIGM). Ct values were calculated from the system's software (BIOMARK™ Real-time PCR Analysis; FLUIDIGM) and filtered according to a set of quality control rules outlined below.

Gene Filter:

(a) For each gene, including controls, data with CtCall=FAILED and CtQuality<threshold were removed.

(b) For each gene, including controls, CtValues>=32.0 were removed to filter out very low expression genes.

(c) For each gene, including controls, genes with a difference of duplicate CtValues>=2.0 were considered inconsistent and removed.

Sample Filter:

(a) If the control gene (Gapdh) was not expressed or was removed according to gene filters (a-c), the whole sample was removed.

(b) If the mean of the Ct values of all genes in a row was >=27.0 the whole sample row was removed.

Time-Lapse Imaging and Analysis:

Wherever possible our video microscopy protocols followed proposed guidelines[24]. In detail, FACS sorted CD150+ CD34− KSLF HCS from wt C57/Bl6 or GFP-negative CD150+ CD34− KSLF HSC from PU.1-GFP reporter mouse[31] bone marrow were suspended in SCM supplemented with 100 U/ml penicillin and 100 mg/ml streptomycin, 20 ng/ml rSCF, 50 ng/ml rTPO+/−100 ng/ml rM-CSF and plated in Ibidi µ-slidesVI(0.4) (Biovalley SA, France). Time-lapse microscopy was performed using a Cell Observer system (Carl Zeiss Microscopy GmbH, Germany) at 37° C. and 5% CO2. Images were acquired every 10 minutes using 10× (A-plan 10×/0.45 Ph1) or 40× (Plan-Apochromat 40×/0.95 Korr M27) objectives in brightfield and fluorescence (GFP filters: EX BP 470/40; at 350 ms) with a COOLSNAP™ HQ2 monochrome camera (Photometrics) with a 2×2 binning and a metal halide 120W source for fluorescence illumination. For image analysis a matrix of 4×4 images was acquired for each time point. Images were stitched with AxioVision software (Carl Zeiss Microscopy GmbH, Germany) and processed with Fiji software[36] using a slight rolling ball subtraction of background and 1 pixel Gaussian blur. For background subtraction of brightfield images, the median of z-projection was subtracted from the time-lapse stack. Single cell tracking was performed with basic commands of ImageJ[37] and Fiji[36] software and with specific tracking plugin MTrackJ[38] in manual mode. Each cell was tracked manually frame-by-frame in the bright field channel and cross-controlled by two microscope specialists. Cells with non-standard morphology or size were rejected. The fluorescence signal was measured as the difference of maximum minus minimum intensity within a defined region of interest (ROI) around each cell. Cell properties and behaviour (cell division, cell death, position, fluorescence increase) were manually documented to build cumulated curves. R[39] and Excel (Microsoft Corporation) software was used to manage data and build graphics.

Statistical Analysis:

P values were calculated by two-tailed non parametric Mann-Witney test for direct sample comparisons or Pearson's chi$^2$ test for proportions (alpha=0.05). Whisker plots show median (lines), upper and lower quartiles (boxes) and extreme outliers (dotted whiskers).

Results

Lineage specific cytokines such as macrophage colony stimulating factor (M-CSF), can be strongly induced during physiological stress or infection[10,11]. and increase the production of mature cells from lineage-committed progenitors[1,2]. According to the prevailing model, however, they are generally not believed to directly influence differentiation decisions of haematopoietic stem cells (HSC)[9,12,13]. Cell fate choice of HSC has traditionally been explained by stochastic models[14]. In this view transcriptional noise[15] and random variations in competing lineage determining transcription factors lead to cross-antagonistic switches that initiate lineage choice[4,5,6,7], whereas cytokines are thought to only act on the resulting progeny cells by stimulating their survival and proliferation[8,9]. A key example of such a master regulator is the transcription factor PU.1 that induces myelo-monocytic differentiation[16,17]. It is generally unknown whether external signals could drive the initial activation of such intrinsic master regulators. Since HSC deficient for the transcription factor MafB are sensitized to PU.1 activation in response to M-CSF[3], we have investigated whether high systemic M-CSF levels could induce PU.1 and instruct myelo-monocytic fate in wt HSC without prior modification of transcription factor balance.

We observed that lipopolysacharide (LPS), a strong mimetic of bacterial infection stimulating high systemic levels of M-CSF[11], induced an up-regulation of GFP in long term HSC (CD117+sca+Lin-CD135-CD34-CD150+) of PU.1-GFP reporter mice[18]. Consistent with the expression of the M-CSF receptor (M-CSFR) in HSC[3,19] direct intravenous injection of recombinant M-CSF also induced significantly increased PU.1 activation in HSC after 16 h (FIG. 1a,b). The treatment caused no significant change in M-CSFR or MafB expression, arguing against selection of myeloid primed HSC with high M-CSFR or low MafB levels. M-CSF also induced no change in the proportion of CD150$^{hi}$ HSC, reported to have myeloid lineage bias[20], in GFP-positive or -negative HSC and activated PU.1 to a similar extent in CD150$^{hi}$ HSC (FIG. 1c) as in total HSC (FIG. 1a,b). Finally cultured CD150$^{hi}$ HSC revealed no proliferation or survival advantage in the presence of M-CSF. Together these data argued against selective amplification or survival of a pre-existing HSC sub-population and indicated that M-CSF could newly induce PU.1 expression in HSC.

As shown in FIG. 1d, the M-CSF effect on stem cells was direct and specific, since FACS purified HSC showed increased PU.1 expression after 16 h in culture with M-CSF but not with GM-CSF or G-CSF, cytokines that may also be released during infection[22]. The observed changes in gene expression cannot be explained by M-CSF dependent selection of PU.1+ cells, as video-microscopy of cultured HSC showed no proliferation or survival advantage in M-CSF and PU.1 was induced before onset of cell division. Continuous observation of individual GFP-negative sorted HSC from PU.1-GFP mice by video imaging confirmed that M-CSF could induce PU.1 expression in previously PU.1 negative cells (FIG. 2a-c). We recorded the fate of HSC between 18 hours and 42 hours of culture, when both the induction of PU.1 in previously negative cells and the division of PU.1+ cells could theoretically occur. At the end of the 24 h observation period over two-fold more PU.1+ cells had developed in M-CSF than under control conditions (FIG. 2d) and backtracking the origin of these cells revealed that all PU.1+ cells were derived from previously PU.1 negative cells, but none from divisions of PU.1+ cells. Although the absence of PU.1+ cell division may be partially due to the phototoxic effects of GFP excitement[23,24], we could conclude that the observed increase in PU.1+ cells was entirely due to M-CSF induced activation of the PU.1 reporter. These commitment events of PU.1 activation occurred 8 hours earlier and at a higher rate over the whole observation period in the presence of M-CSF (FIG. 2e). Our results indicated that M-CSF could directly increase PU.1 promoter activation in single, previously PU.1 negative HSC.

To further investigate whether M-CSF induced PU.1 activation changed the cell identity of individual HSC we analyzed the mRNA expression profile of single cells by nanofluidic real time PCR on FLUIDIGM™ dynamic arrays. Consistent with their stem cell identity almost all freshly isolated HSC expressed stem and progenitor cell associated genes and about half expressed either no (lin-) or multiple lineage specific genes (mix). The remainder showed mainly megakaryocytic (Meg), megakaryocytic-erythroid (MegE) or myeloid lineage priming. Culture for 16 h without M-CSF led to an increased number of cells with a mixed lineage profile at the expense of Meg and lin-profiles. By contrast, culture in the presence of M-CSF induced a strong increase of cells with a myeloid gene expression signature. Consistent with the video microscopy results the increase in myeloid gene expression was associated with a doubling of the number of PU.1+ cells. Interestingly, this increase was entirely due to PU.1+ cells with a myeloid signature that did not express genes from any other lineage. By contrast, the number of PU.1+ cells that also expressed non-myeloid genes remained approximately constant (FIG. 3a). Together this indicated that M-CSF induced PU.1+ cells had assumed a myeloid cell identity. To evaluate whether this change in gene expression reflected a functional myeloid lineage choice in vivo we compared the differentiation potential of unstimulated PU.1- HSC to PU.1- and PU.1+ HSC after in vivo priming with M-CSF (FIG. 3b). Progenitor analysis in the spleen 2 weeks after transplantation of these populations revealed a higher ratio of granulocyte/macrophage progenitors (GMP) to megakaryocytic/erythroid progenitors (MEP) developing from PU.1+ HSC than from PU.1- HSC (FIG. 3c,d). We observed a similar increase in myeloid differentiation potential for PU.1+ cells derived from M-CSF stimulated PU.1- HSC in culture (FIG. 5a-c). Together these data showed that M-CSF induced PU.1 led to a myeloid cell fate change in single HSC.

To further investigate, whether M-CSF could also induce a cell fate change of individual HSC in vivo, we transplanted CFSE-labelled HSC into the spleen, a site of extra-medullary haematopoiesis with adapted stem cell niches[3,25], and analyzed expression of endogenous PU.1 protein by immuno-fluorescence in single HSC after 24 h. Whereas the vast majority of HSC were PU.1 negative immediately after transplantation, nearly all had activated PU.1 after transfer into spleens of LPS challenged hosts. This effect was principally dependent on M-CSF signalling as a blocking antibody against the M-CSF receptor[26] strongly inhibited PU.1 activation. Furthermore, direct injection of recombinant M-CSF resulted in a similar strong induction of PU.1 in the transplanted HSC. This effect appeared to be entirely cell autonomous, as M-CSF receptor deficient (M-CSFR$^{-/-}$)[27] HSC showed no higher activation of PU.1 in M-CSF stimulated than control recipients. Similarly, small molecule inhibitors of the M-CSFR or PI3K, ERK and SRC kinases that signal downstream of the receptor[28] also prevented induction of PU.1, consistent with the stimulation of transcriptional activators of the pu.1 gene by these pathways. Furthermore, transplantation of in vivo M-CSF primed CD45.2 HSC into sub-lethally irradiated CD45.1 recipients revealed an increased ratio of GMP to MEP progenitors in the spleen after 2 weeks (FIG. 4a, FIG. 6a,b) and an increased myeloid to lymphoid cell ratio in peripheral blood after 4 weeks (FIG. 6c). In competitive transplantation assays M-CSF primed HSC also showed a myeloid advantage compared to platelet and lymphoid contribution at 4 weeks in the blood that re-equilibrated after 6 weeks and did not compromise long-term multi-lineage contribution (FIG. 4b, FIG. 7). Finally, this myeloid differentiation preference of M-CSF primed HSC could be abolished by deletion of PU.1 (FIG. 4c). Together these results indicated that M-CSF could directly instruct a change in cell identity of single HSC in vivo that resulted in a reversible, PU.1-dependent myeloid differentiation preference.

Our results show that under haematopoietic stress conditions of infection high systemic levels of M-CSF can directly instruct myeloid gene expression and differentiation preference of HSC. This challenges both the current view of cytokine action and how HSC make differentiation decision. Whereas cytokines are commonly thought to act on lineage-committed progenitors, we here show that stem cells are direct targets of lineage instruction by cytokines. HSC have been shown to proliferate in response to signals characteristic of bacterial[29] or viral infections[30] but without changing lineage specific gene expression or differentiation potential. In line with the prevailing paradigm of selective cytokine action it has been proposed that distinct stem cell subtypes could have a selective advantage in response to different stimuli[21]. Such a mechanism is difficult to distinguish from instructive mechanisms on a population basis. We have here employed multiple assays of single cell analysis in culture and in vivo in a time window before the onset of cell division to distinguish induced changes of lineage specification from selective mechanisms. These data indicate that M-CSF can directly change stem cell identity by activation of the myeloid master regulator PU.1 on the promoter, message and protein level, independently of selective survival or proliferation. The multi-lineage priming of gene expression in haematopoietic stem cells has generally been interpreted as indication that initial cell fate decisions are driven solely by stochastic fluctuations in the balance of lineage specific transcription factors[4,5,6,12,13]. Our data now indicate that cytokines can not only amplify random choices but also directly activate key regulators of lineage specification such as PU.1 to instruct lineage fate of haematopoietic stem cells to induce an insult tailored output of progeny. As M-CSF treatment can transiently increase the production of myeloid progeny without compromising stem cell activity, it may be useful to ameliorate myeloid cytopenias, particularly to protect patients from infection after stem cell transplantation.

EXAMPLES 2 & 3

Functional Impact of MCSF

To study the functional impact of MCSF mediated HSC commitment during infections, two separate series of experiments were performed. In all experiments, after lethal irradiation of recipients, 2500 HS/PC with 200,000 cKit-carrier cells from donors were grafted. Uninfected and not transplanted mice served as controls to demonstrate that irradiation was lethal (dotted black line; FIGS. 8A, 8B and FIGS. 10A, 10B; n=12).

Uninfected mice that received HS/PC transplants served as controls for efficient life saving transplantation (black line; FIGS. 8A, 8B and FIGS. 10A, 10B; n=8). Two other groups of mice received either 3 injections of MCSF (rh-MCSF or Bacculo virus produced mMCSF) or PBS on the day of HS/PC transplantation.

One-week post transplantation these mice were challenged with lethal doses of either the bacteria *Pseudomonas aeruginosa* or the opportunistic fungus *Aspergillus fumigatus*.

EXAMPLE 2

MCSF Stimulation Following HS/PC Transplantation Protects Against Bacterial Infection Material & Methods
Mice:
CD45.1 and C57Bl/6 mice were obtained from Charles River. 10-14 weeks old sex-matched CD45.2 recipients were reconstituted as described[3] with bone marrow derived KSL (c-Kit(CD117)+, Sca+, Lin−) HS/PC isolated from 6-8 weeks old CD45.1. For in vivo injections the indicated concentrations of M-CSF and/or sorted cells were injected in 100-200 μl of PBS into the retro-orbital sinus. For HS/PC transplantation 2500 KLS HS/PC were sorted from CD45.1 mice and mixed with 200,000 cKit− CD45.2 or cKit−, Terr119+ carrier cells prior to injection into lethally irradiated (160 kV, 25 mA, 6.31 Gy) CD45.2 recipient mice. After irradiation all mice were given antibiotics in the drinking water to reduce the chance of opportunistic infection with other pathogens. (All mouse experiments were performed under specific pathogen-free conditions in accordance with institutional guidelines).

Isolation of Hematopoietic Stem and Progenitor Cells (HS/PC) and cKit-Cells:

Total bone marrow cells were depleted of mature cells by staining with biotinylated rat antimouse lineage antibody cocktail, followed by streptavidin immuno-magnetic micro beads (Miltenyi Biotec). Lineage negative cells were stained with HS/PC markers: anti-CD117-APC-H7 (clone 2B8, BD Biosciences), anti-Sca-1-PE-Cy5 (clone D7, Bio legend), Streptavidin-APC (eBioscience) and LIVE/DEAD Fixable Violet Dead cell dye (Invitrogen) as viability marker. HS/PC were sorted using FACSAriaIII equipment. For isolating cKit-carrier cells, whole bone marrow cells were depleted of cKit+ cells by staining with biotinylated antimouse CD117 (clone 2B8, BioLegend), followed by streptavidin immuno-magnetic micro beads (Miltenyi Biotec) and negative cells were sorted using automacs. For Terr119+ carrier cells, the cKit-cells were incubated with biotinylated anti-Ter119 followed by anti-biotin microbeads and positively sorted using automacs.

M-CSF Treatment:

Each mouse received three injections of 10 μg M-CSF: 1 h before HS/PC transplantation; 6 h and 18 h post-transplantation. Human M-CSF (rhMCSF, Chiron Corporation Inc., USA, now part of Novartis AG) and Mouse M-CSF was expressed in baculovirus (Bac. virus mMCSF[56]) were used for the study.

Infection with *Pseudomonas aeruginosa*:

The *P. aeruginosa* PA14 strain was tagged with green fluorescent protein (GFP), as described elsewhere[53,54]. The GFP-tagged PA14 strain was cultured overnight at 37° C. in LB, diluted 1:100 in LB and grown for 3 hrs to reach bacterial exponential phase (3 to 4 OD600 nm). A volume of 100 μl of a bacterial solution of 5×103 CFU/ml diluted in PBS was further used for infection studies. One-week post-HS/PC transplantation mice were challenged by intra-peritoneal inoculation of 500 Colony Forming Units (CFUs) of bacteria in 100 μL of sterile PBS.

Bacterial Tissue Load Quantification:

The infected mice were killed; the organs (spleen, lungs, liver and heart) were harvested and weighed. To determine CFUs per gram of tissue serial dilutions of tissue homogenates were prepared in PBS and plated on *Pseudomonas* Isolation Agar (PIA) (Difco laboratories) supplemented with appropriate antibiotics and incubated overnight at 37° C. The colonies were counted after 16-24 h.

Results

MCSF Stimulation Following HS/PC Transplantation Protects Against *Pseudomonas aeruginosa* Infection and Reduced Bacterial Tissue Load.

Following irradiation and HS/PC transplantation, mice were infected with *P. aeruginosa* on Day8 (D8). Mice that were treated with human MCSF showed improved survival (triangle line; FIG. 8A; n=10) from 15.3% in untreated (square line) to 50% in MCSF treated mice (triangle line, FIGS. 8A and B; n=13). Mice that were treated with mouse MCSF showed further enhanced survival to 87.5% (triangle line; FIG. 8B; n=8).

Furthermore in the mice succumbing to infection death was delayed in the M-CSF treated mice (FIGS. 8A and B).

For analysis of bacterial load, mice were killed at 18 h after infection, tissue homogenates were prepared from spleen, lungs, liver and heart, and were plated to determine CFU. Eight to ten of the 13 mice in the untreated group were moribund compared with two to three of the 10 mice in the rhMCSF treated group. At this earlier time point, rhMCSF treated mice showed significant decrease in the tissue load of bacteria when compared with the untreated mice (FIG. 9) suggesting that increased survival was due to a reduction in bacterial load.

EXAMPLE 3

MCSF Stimulation Following HS/PC Transplantation Protects Against Fungal Infection Material & Methods Mice; Isolation of Hematopoietic Stem and Progenitor Cells (HS/PC) and cKit-Cells & M-CSF Treatment:

As described above in EXAMPLE 2.

Infection with *Aspergillus* Fumigates:

*Aspergillus fumigatus* FGSC 1100 was provided by the Centre International de Ressources Microbiennes—Champignons Filamenteux (CIRM-CF, Marseille, France). For each experiment, cultures were grown on Malt agar medium (2% malt extract, 2% Bacto-agar DIFCO) for 5 days at 25° C. Conidial suspension was prepared in sterile saline according to Bitmansour et al. (2002)[55]. One-week post-HS/PC transplantation mice were infected by intranasal inoculation of $2-4\times10^6$ conidia in 20-40 μL of sterile PBS.

Fungal Culture of Infected Organs:

The organs (lungs, liver, heart and spleen) were harvested, weighed and tissue homogenates were prepared in PBS. The homogenates were serially diluted and 200 μL or each dilution was plated on Sabouraud dextrose agar (DIFCO). The plates were incubated at 25° C. and pictures were taken after 3-5 days.

Results

MCSF Stimulation Following HS/PC Transplantation Protects Against *Aspergillus fumigatus* Infection and Reduces Fungal Tissue Load.

Post-irradiation and HS/PC transplantation, mice were infected with *A. fumigatus* on D8. Mice treated with human MCSF showed 40% survival (triangle line; FIG. 10A; n=10) compared to untreated mice, which showed only 10% survival (square line; FIGS. 10A and B; n=10). Interestingly, mice that were treated with mouse MCSF were further protected and showed 60% survival (triangle line; FIG. 10B; n=10). One among 10 mice in the untreated group that survived for 6 days after infection remained alive during the total 35-day observation period.

Furthermore in the mice succumbing to infection death was slightly delayed from D9-D14 in untreated mice to D10-D15 in the rhMCSF treated group. For analysis of fungal load, mice were killed at 48 h after infection and tissue homogenates were prepared from lungs, liver and heart. Diluted homogenates (1/10 of lung, liver and heart; 1/100 of heart) were plated on Sabouraud dextrose agar plates to observe fungal colony growth. rhMCSF treated mice showed significant decrease in the tissue load of fungal colonies when compared with the untreated mice. Fungal tissue cultures were incubated beyond 96 h to verify the typical colony morphology of *A. fumigatus*.

REFERENCES

Throughout this application, various references describe the state of the art to which this invention pertains. The disclosures of these references are hereby incorporated by reference into the present disclosure.

[1] Metcalf, D. Hematopoietic cytokines. *Blood* 111, 485-491 (2008).
[2] Rieger, M. A. Hoppe, P. S., Smejkal, B. M. Eitelhuber, A. C. & Schroeder, T. Hematopoietic cytokines can instruct lineage choice. *Science* 325, 217-218 (2009).
[3] Sarrazin, S. et al. MafB restricts M-CSF dependent myeloid commitment divisions of hematopoietic stem cells *Cell* 138, 1-14 (2009).
[4] Orkin, S. H. Diversification of haematopoietic stem cells to specific lineages. *Nat Rev Genet* 1, 57-64 (2000).
[5] Cantor, A. B. & Orkin, S. H. Hematopoietic development: a balancing act. *Curr Opin Genet Dev* 11, 513-519 (2001).
[6] Enver, T., Pera, M., Peterson, C. & Andrews, P. W. Stem cell states, fates, and the rules of attraction. *Cell Stem Cell* 4, 387-397(2009).
[7] Graf, T. & Enver, T. Forcing cells to change lineages. *Nature* 462, 587-594 (2009).
[8] Socolovsky, M., Lodish, H. F. & Daley, G. Q. Control of hematopoietic differentiation: lack of specificity in signaling by cytokine receptors. *Proc Natl Acad Sci USA* 95, 6573-6575 (1998).
[9] Metcalf, D. On hematopoietic stem cell fate. *Immunity* 26, 669-673 (2007).
[10] Cheers, C. & Stanley, E. R. Macrophage production during murine listeriosis: colony-stimulating factor 1 (CSF-1) and CSF-1-binding cells in genetically resistant and susceptible mice. *Infect Immun* 56, 2972-2978 (1988).
[11] Roth, P., Bartocci, A. & Stanley, E. R. Lipopolysaccharide induces synthesis of mouse colony-stimulating factor-1 in vivo. *J Immunol* 158, 3874-3880 (1997).
[12] Cross, M. A. & Enver, T. The lineage commitment of hemopoietic progenitor cells. *Curr Opin Genet Dev* 7, 609-613(1997).
[13] Enver, T., Heyworth, C. M. & Dexter, T. M. Do stem cells play dice? *Blood* 92, 348-351(1998).
[14] Till, J. E., McCulloch, E. A. & Siminovitch, L. A Stochastic Model of Stem Cell Proliferation, Based on the Growth of Spleen Colony-Forming Cells. *Proc Natl Acad Sci USA* 51, 29-36 (1964).

[15] Chang, H. H., Hemberg, M., Barahona, M., Ingber, D. E. & Huang, S. Transcriptome-wide noise controls lineage choice in mammalian progenitor cells. *Nature* 453, 544-547 (2008).

[16] Laiosa, C. V., Stadtfeld, M. & Graf, T. Determinants of lymphoid-myeloid lineage diversification. *Annu Rev Immunol* 24, 705-738 (2006).

[17] Orkin, S. H. & Zon, L. I. Hematopoiesis: an evolving paradigm for stem cell biology. *Cell* 132, 631-644 (2008).

[18] Back, J., Allman, D., Chan, S. & Kastner, P. Visualizing PU.1 activity during hematopoiesis. *Exp Hematol* 33, 395-402 (2005).

[19] Miyamoto, T. et al. Myeloid or lymphoid promiscuity as a critical step in hematopoietic lineage commitment. *Dev Cell* 3, 137-147 (2002).

[20] Morita, Y., Ema, H. & Nakauchi, H. Heterogeneity and hierarchy within the most primitive hematopoietic stem cell compartment. *J Exp Med* 207, 1173-1182 (2010).

[21] King, K. Y. & Goodell, M. A. Inflammatory modulation of HSCs: viewing the HSC as a foundation for the immune response. *Nat Rev Immunol* 11, 685-692 (2011).

[22] Cheers, C. et al. Production of colony-stimulating factors (CSFs) during infection: separate determinations of macrophage-, granulocyte-, granulocyte-macrophage-, and multi-CSFs. *Infect Immun* 56, 247-251 (1988).

[23] Hoebe, R. A. et al. Controlled light-exposure microscopy reduces photobleaching and phototoxicity in fluorescence live-cell imaging. *Nat Biotechnol* 25, 249-253 (2007).

[24] Schroeder, T. Long-term single-cell imaging of mammalian stem cells. *Nat Methods* 8, S30-35 (2011).

[25] Kiel, M. J. & Morrison, S. J. Uncertainty in the niches that maintain haematopoietic stem cells. *Nat Rev Immunol* 8, 290-301 (2008).

[26] Sudo, T. et al. Functional hierarchy of c-kit and c-fms in intramarrow production of CFU-M. *Oncogene* 11, 2469-2476 (1995).

[27] Dai, X. M. et al. Targeted disruption of the mouse colony-stimulating factor 1 receptor gene results in osteopetrosis, mononuclear phagocyte deficiency, increased primitive progenitor cell frequencies, and reproductive defects. *Blood* 99, 111-120 (2002).

[28] Pixley, F. J. & Stanley, E. R. CSF-1 regulation of the wandering macrophage: complexity in action. *Trends Cell Biol* 14, 628-638 (2004).

[29] Baldridge, M. T., King, K. Y., Boles, N. C., Weksberg, D. C. & Goodell, M. A. Quiescent haematopoietic stem cells are activated by IFN-gamma in response to chronic infection. *Nature* 465, 793-797(2010).

[30] Essers, M. A. et al. IFNalpha activates dormant haematopoietic stem cells in vivo. *Nature* 458, 904-908 (2009).

[31] Back, J., Dierich, A., Bronn, C., Kastner, P. & Chan, S. PU.1 determines the self-renewal capacity of erythroid progenitor cells. *Blood* 103, 3615-3623 (2004).

[32] Dakic, A. et al. PU.1 regulates the commitment of adult hematopoietic progenitors and restricts granulopoiesis. *J Exp Med* 201, 1487-1502 (2005).

[33] Okabe, M., Ikawa, M., Kominami, K., Nakanishi, T. & Nishimune, Y. 'Green mice' as a source of ubiquitous green cells. *FEBS Lett* 407, 313-319 (1997).

[34] Bryder, D., Rossi, D. J. & Weissman, I. L. Hematopoietic stem cells: the paradigmatic tissue-specific stem cell. *Am J Pathol* 169, 338-346 (2006).

[35] Niu, C. et al. c-Myc is a target of RNA-binding motif protein 15 in the regulation of adult hematopoietic stem cell and megakaryocyte development. *Blood* 114, 2087-2096(2009).

[36] Schindelin, J., Proceedings of the ImageJ conference (2008).

[37] Rasband, W. S., ImageJ, http://imagej.nih.gov/ij/ (Bethesda, M L, USA, 1997-2012).

[38] Meijering, E., Dzyubachyk, O. & Smal, I. Methods for cell and particle tracking. *Methods Enzymol* 504, 183-200 (2012).

[39] R: A language and environment for statistical computing (Vienna, Austria, 2012).

[40] Laslo, P. et al. Multilineage transcriptional priming and determination of alternate hematopoietic cell fates. *Cell* 126, 755-766 (2006).

[41] Pronk, C. J. et al. Elucidation of the phenotypic, functional, and molecular topography of a myeloerythroid progenitor cell hierarchy. *Cell Stem Cell* 1, 428-442 (2007).

[42] McCubrey, J. A. et al. Roles of the RAF/MEK/ERK and PI3K/PTEN/AKT pathways in malignant transformation and drug resistance. *Adv Enzyme Regul* 46, 249-279, (2006).

[43] Jack, G. D., Zhang, L. & Friedman, A. D. M-CSF elevates c-Fos and phospho-C/EBPalpha(S21) via ERK whereas G-CSF stimulates SHP2 phosphorylation in marrow progenitors to contribute to myeloid lineage specification. *Blood* 114, 2172-2180, (2009).

[44] Bae, S. C. & Lee, Y. H. Phosphorylation, acetylation and ubiquitination: the molecular basis of RUNX regulation. *Gene* 366, 58-66, (2006).

[45] Buitenhuis, M. & Coffer, P. J. The role of the PI3K-PKB signaling module in regulation of hematopoiesis. *Cell Cycle* 8, 560-566, (2009).

[46] Lichtinger, M. et al. RUNX1 reshapes the epigenetic landscape at the onset of haematopoiesis. *EMBO J* 31, 4318-4333, (2012).

[47] Yeamans, C. et al. C/EBPalpha binds and activates the PU.1 distal enhancer to induce monocyte lineage commitment. *Blood* 110, 3136-3142, (2007).

[48] Huang, G. et al. PU.1 is a major downstream target of AML1 (RUNX1) in adult mouse hematopoiesis. *Nat Genet* 40, 51-60, (2008).

[49] Bonadies, N. et al. PU.1 is regulated by NF-kappaB through a novel binding site in a 17 kb upstream enhancer element. *Oncogene* 29, 1062-1072, (2010).

[50] Leddin, M. et al. Two distinct auto-regulatory loops operate at the PU.1 locus in B cells and myeloid cells. *Blood* 117, 2827-2838, (2011).

[51] Zhang, P. et al. Enhancement of hematopoietic stem cell repopulating capacity and self-renewal in the absence of the transcription factor C/EBP alpha. *Immunity* 21, 853-863 (2004).

[52] Steidl, U. et al. Essential role of Jun family transcription factors in PU.1 knockdown-induced leukemic stem cells. *Nat Genet* 38, 1269-1277, (2006).

[53] B. Koch, L. E. Jensen, O. Nybroe, A panel of Tn7-based vectors for insertion of the gfp marker gene or for delivery of cloned DNA into Gram-negative bacteria at a neutral chromosomal site. *J Microbiol Methods* 45, 187 (July, 2001).

[54] C. Giraud et al., The PprA-PprB two-component system activates CupE, the first non-archetypal *Pseudomonas aeruginosa* chaperone-usher pathway system assembling fimbriae. *Environmental microbiology* 13, 666 (March, 2011).

[55] A. Bitmansour et al., Myeloid progenitors protect against invasive aspergillosis and *Pseudomonas aeruginosa* infection following hematopoietic stem cell transplantation. *Blood* 100(13): 4660-7 (December, 2002).

[56] Z. E. Wang et al., Identification of the ligand-binding regions in the macrophage colony-stimulating factor receptor extracellular domain. *Mol Cell Biol.*;13(9):5348-59 (September 1993).

The invention claimed is:

1. A method of treating myeloid cytopenia and an associated viral, bacterial and/or fungal infection in a patient in need thereof, comprising:
increasing production of myeloid cells expressing transcription factor PU.1 in said patient by administering to said patient a therapeutically effective amount of a macrophage colony stimulating factor (M-CSF) polypeptide or an interleukin-34 polypeptide, wherein said patient is undergoing or has undergone hematopoietic stem cell transplantation (HSCT), wherein expression of MafB in cells of a stem cell graft used for the HSCT was not previously modified, and wherein said myeloid cytopenia is neutropenia, monocytopenia and/or cytopenia of monocyte derived mononuclear phagocytes, wherein said myeloid cells comprise granulocyte/monocyte progenitor cells that give rise to granulocytes, monocytes and macrophages.

2. The method according to claim 1, wherein myeloid cytopenia is induced by a myeloablative therapy.

3. The method according to claim 1, wherein the M-CSF polypeptide has the sequence comprising or consisting of SEQ ID NO: 5.

4. The method according to claim 1, further comprising, prior to said increasing step, incubating a hematopoietic stem cell graft to be used for HSCT in the presence of the M-CSF polypeptide or the interleukin-34 polypeptide to produce primed cells and infusing the primed cells into said patient.

5. The method according to claim 1, wherein myeloid cytopenia and an associated viral infection is treated.

6. The method according to claim 5, wherein said viral infection is a cytomegalovirus infection.

7. A method for treating viral, bacterial and/or fungal infections associated with myeloid cytopenia in a patient that is undergoing or has undergone hematopoietic stem cell transplantation (HSCT), comprising:
administering to said patient a therapeutically sufficient amount of an M-CSF polypeptide or an interleukin-34 polypeptide to cause increased production of myeloid cells expressing transcription factor PU.1 in said patient and thereby reduce viral, bacterial and/or viral infections in said patient, wherein expression of MafB in cells of a stem cell graft used for the HSCT was not previously modified, wherein said myeloid cells comprise granulocyte/monocyte progenitor cells.

8. The method of claim 7, wherein said viral, bacterial and/or fungal infection is a cytomegalovirus infection.

9. The method of claim 7, wherein said granulocyte/monocyte progenitor cells give rise to granulocytes, monocytes and macrophages.

10. The method of claim 7, wherein said M-CSF polypeptide comprises or consists of SEQ ID NO. 5.

* * * * *

SEQUENCE LISTING

<160> NUMBER OF SEQ ID NOS: 6

<210> SEQ ID NO 1
<211> LENGTH: 256
<212> TYPE: PRT
<213> ORGANISM: Homo sapiens

<400> SEQUENCE: 1

Met Thr Ala Pro Gly Ala Ala Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Gly His Glu Arg Gln Ser Glu Gly Ser Phe Ser
            180                 185                 190

Pro Gln Leu Gln Glu Ser Val Phe His Leu Leu Val Pro Ser Val Ile
        195                 200                 205

Leu Val Leu Leu Ala Val Gly Gly Leu Leu Phe Tyr Arg Trp Arg Arg
    210                 215                 220

Arg Ser His Gln Glu Pro Gln Arg Ala Asp Ser Pro Leu Glu Gln Pro
225                 230                 235                 240

Glu Gly Ser Pro Leu Thr Gln Asp Asp Arg Gln Val Glu Leu Pro Val
                245                 250                 255

<210> SEQ ID NO 2
<211> LENGTH: 554
<212> TYPE: PRT
<213> ORGANISM: homo sapiens

<400> SEQUENCE: 2

Met Thr Ala Pro Gly Ala Ala Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu

```
                35                  40                  45
Gln Ser Leu Gln Arg Leu Ile Asp Ser Gln Met Glu Thr Ser Cys Gln
             50                  55                  60

Ile Thr Phe Glu Phe Val Asp Gln Glu Gln Leu Lys Asp Pro Val Cys
 65                  70                  75                  80

Tyr Leu Lys Lys Ala Phe Leu Leu Val Gln Asp Ile Met Glu Asp Thr
                 85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
            130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu
210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
450                 455                 460
```

```
Ala Arg Pro Leu Pro Arg Phe Asn Ser Val Pro Leu Thr Asp Thr Gly
465                 470                 475                 480

His Glu Arg Gln Ser Glu Gly Ser Ser Pro Gln Leu Gln Glu Ser
            485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Ser His Gln Glu Pro
            515                 520                 525

Gln Arg Ala Asp Ser Pro Leu Glu Gln Pro Glu Gly Ser Pro Leu Thr
            530                 535                 540

Gln Asp Asp Arg Gln Val Glu Leu Pro Val
545                 550

<210> SEQ ID NO 3
<211> LENGTH: 438
<212> TYPE: PRT
<213> ORGANISM: Homo sapiens

<400> SEQUENCE: 3

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
```

```
                275                 280                 285
Pro Gly Met Glu Asp Ile Leu Asp Ser Ala Met Gly Thr Asn Trp Val
    290                 295                 300
Pro Glu Glu Ala Ser Gly Ala Ser Glu Ile Pro Val Pro Gln Gly
305                 310                 315                 320
Thr Glu Leu Ser Pro Ser Arg Pro Gly Gly Ser Met Gln Thr Glu
                325                 330                 335
Pro Ala Arg Pro Ser Asn Phe Leu Ser Ala Ser Ser Pro Leu Pro Ala
            340                 345                 350
Ser Ala Lys Gly Gln Gln Pro Ala Asp Val Thr Gly His Glu Arg Gln
            355                 360                 365
Ser Glu Gly Ser Ser Pro Gln Leu Gln Glu Ser Val Phe His Leu
    370                 375                 380
Leu Val Pro Ser Val Ile Leu Val Leu Leu Ala Val Gly Gly Leu Leu
385                 390                 395                 400
Phe Tyr Arg Trp Arg Arg Arg Ser His Gln Glu Pro Gln Arg Ala Asp
                405                 410                 415
Ser Pro Leu Glu Gln Pro Glu Gly Ser Pro Leu Thr Gln Asp Asp Arg
            420                 425                 430
Gln Val Glu Leu Pro Val
            435

<210> SEQ ID NO 4
<211> LENGTH: 156
<212> TYPE: PRT
<213> ORGANISM: Artificial
<220> FEATURE:
<223> OTHER INFORMATION: Recombinant murine M-CSF fragment of 156 amino
      acids

<400> SEQUENCE: 4

Met Lys Glu Val Ser Glu His Cys Ser His Met Ile Gly Asn Gly His
1               5                   10                  15
Leu Lys Val Leu Gln Gln Leu Ile Asp Ser Gln Met Glu Thr Ser Cys
            20                  25                  30
Gln Ile Ala Phe Glu Phe Val Asp Gln Glu Gln Leu Asp Asp Pro Val
        35                  40                  45
Cys Tyr Leu Lys Lys Ala Phe Phe Leu Val Gln Asp Ile Ile Asp Glu
    50                  55                  60
Thr Met Arg Phe Lys Asp Asn Thr Pro Asn Ala Asn Ala Thr Glu Arg
65                  70                  75                  80
Leu Gln Glu Leu Ser Asn Asn Leu Asn Ser Cys Phe Thr Lys Asp Tyr
                85                  90                  95
Glu Glu Gln Asn Lys Ala Cys Val Arg Thr Phe His Glu Thr Pro Leu
            100                 105                 110
Gln Leu Leu Glu Lys Ile Lys Asn Phe Phe Asn Glu Thr Lys Asn Leu
        115                 120                 125
Leu Glu Lys Asp Trp Asn Ile Phe Thr Lys Asn Cys Asn Asn Ser Phe
    130                 135                 140
Ala Lys Cys Ser Ser Arg Asp Val Val Thr Lys Pro
145                 150                 155

<210> SEQ ID NO 5
<211> LENGTH: 150
<212> TYPE: PRT
<213> ORGANISM: Artificial
<220> FEATURE:
```

<223> OTHER INFORMATION: Recombinant human M-CSF fragment of 150 amino acids

<400> SEQUENCE: 5

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys
145             150
```

<210> SEQ ID NO 6
<211> LENGTH: 242
<212> TYPE: PRT
<213> ORGANISM: Homo sapiens

<400> SEQUENCE: 6

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190
```

```
Val Pro Ser Pro Gln Ser Cys Ser Pro Glu Pro Ser Leu Gln Tyr Ala
        195             200             205

Ala Thr Gln Leu Tyr Pro Pro Pro Trp Ser Pro Ser Ser Pro Pro
    210             215             220

His Ser Thr Gly Ser Val Arg Pro Val Arg Ala Gln Gly Glu Gly Leu
225             230             235             240

Leu Pro
```